US008738296B2

(12) United States Patent
Halpern et al.

(10) Patent No.: US 8,738,296 B2
(45) Date of Patent: May 27, 2014

(54) INDEXING A REFERENCE SEQUENCE FOR OLIGOMER SEQUENCE MAPPING

(75) Inventors: Aaron L. Halpern, San Carlos, CA (US); Igor Nazarenko, Sunnyvale, CA (US)

(73) Assignee: Complete Genomics, Inc., Mountain View, CA (US)

( * ) Notice: Subject to any disclaimer, the term of this patent is extended or adjusted under 35 U.S.C. 154(b) by 421 days.

(21) Appl. No.: 12/698,986

(22) Filed: Feb. 2, 2010

(65) Prior Publication Data

US 2010/0287165 A1 Nov. 11, 2010

Related U.S. Application Data

(60) Provisional application No. 61/149,665, filed on Feb. 3, 2009.

(51) Int. Cl.
*G01N 33/48* (2006.01)
*G06F 19/22* (2011.01)

(52) U.S. Cl.
CPC .................................... *G06F 19/22* (2013.01)
USPC ........................................................... 702/19

(58) Field of Classification Search
CPC ............................... G06F 19/22; G06F 19/28
See application file for complete search history.

(56) References Cited

U.S. PATENT DOCUMENTS

| | | | |
|---|---|---|---|
| 5,577,249 A | 11/1996 | Califano | |
| 5,795,782 A | 8/1998 | Church et al. | |
| 6,015,714 A | 1/2000 | Baldarellie et al. | |
| 6,055,526 A | 4/2000 | Ambroziak | |
| 6,210,891 B1 | 4/2001 | Nyren et al. | |
| 6,306,597 B1 | 10/2001 | Macevicz | |
| 6,309,824 B1 | 10/2001 | Dmanac | |
| 6,401,043 B1 | 6/2002 | Stanton et al. | |
| 6,401,267 B1 | 6/2002 | Drmanac | |
| 6,403,312 B1 | 6/2002 | Dahiyat et al. | |
| 6,627,067 B1 | 9/2003 | Branton et al. | |
| 6,653,072 B1 | 11/2003 | Patten et al. | |
| 6,775,622 B1 | 8/2004 | Holloway | |
| 6,828,100 B1 | 12/2004 | Ronaghi | |
| 6,833,246 B2 | 12/2004 | Balasubramanian | |
| 6,864,052 B1 | 3/2005 | Drmanac et al. | |
| 6,911,345 B2 | 6/2005 | Quake et al. | |
| 7,058,515 B1 | 6/2006 | Selifonov et al. | |
| 7,238,485 B2 | 7/2007 | Akeson et al. | |
| 7,258,838 B2 | 8/2007 | Li et al. | |
| 7,329,496 B2 | 2/2008 | Dower et al. | |
| 2003/0064382 A1 | 4/2003 | Preparata et al. | |
| 2003/0186226 A1 | 10/2003 | Brennan et al. | |
| 2003/0235854 A1 | 12/2003 | Chan et al. | |
| 2004/0018525 A1 | 1/2004 | Wirtz et al. | |
| 2005/0112590 A1 | 5/2005 | Boom et al. | |
| 2005/0149272 A1 | 7/2005 | Pe'er et al. | |
| 2005/0187916 A1 | 8/2005 | Levin et al. | |
| 2005/0202501 A1 | 9/2005 | Yamamoto et al. | |
| 2006/0073501 A1 | 4/2006 | Van Den Boom et al. | |
| 2006/0286566 A1 | 12/2006 | Lapidus et al. | |
| 2006/0287833 A1 | 12/2006 | Yakhini | |
| 2007/0099208 A1 | 5/2007 | Drmanac et al. | |
| 2007/0122817 A1 | 5/2007 | Church et al. | |
| 2007/0225918 A1 | 9/2007 | Sayood et al. | |
| 2008/0040045 A1 | 2/2008 | Selifonov et al. | |
| 2008/0234136 A1 | 9/2008 | Drmanac et al. | |
| 2008/0256070 A1 | 10/2008 | Inglis | |
| 2008/0279892 A1 | 11/2008 | Jin et al. | |
| 2008/0318795 A1 | 12/2008 | Selifonov et al. | |
| 2009/0029477 A1 | 1/2009 | Meller et al. | |
| 2009/0075343 A1 | 3/2009 | Sparks et al. | |
| 2009/0111115 A1 | 4/2009 | Drmanac et al. | |
| 2009/0111705 A1 | 4/2009 | Sparks et al. | |
| 2009/0111706 A1 | 4/2009 | Sparks et al. | |
| 2009/0264299 A1 | 10/2009 | Drmanac et al. | |

FOREIGN PATENT DOCUMENTS

| | | | |
|---|---|---|---|
| WO | 99/52046 A2 | 10/1999 | |
| WO | WO 2006/073504 A2 | 7/2006 | |
| WO | WO 2007/120208 A2 | 10/2007 | |
| WO | WO 2009/155443 A2 | 12/2009 | |
| WO | WO 2010/091021 A2 | 8/2010 | |
| WO | WO 2010/091023 A2 | 8/2010 | |
| WO | WO 2010/091024 A1 | 8/2010 | |
| WO | WO 2010/127045 A2 | 11/2010 | |

OTHER PUBLICATIONS

Venter et al. "The Sequence of the Human Genome" (Science, vol. 291 (2001) pp. 1304-1351).*
International Search Report and Written Opinion corresponding to the PCT application No. PCT/US10/22907, date of mailing Nov. 30, 2010, 9 pages total.
International Search Report and Written Opinion corresponding to the PCT application No. PCT/US10/22913, date of mailing Mar. 16, 2010, 9 pages total.
International Search Report and Written Opinion corresponding to the PCT application No. PCT/US10/32851, date of mailing Nov. 18, 2010, 13 pages total.
Annexstein, "*Generating De Bruijn Sequences: An Efficient Implementation*", IEEE Transactions on Computers, Feb. 1997, (Retrieved from the Internet on Nov. 1, 2010<URL:http://www.computer.org> 46(2):198-200).
Chan et al., "*On the Complexities of de Bruijn Sequences*". Journal of Combinatorial Theory, Series A 1982, 33(3):233-246.
Dahiyat et al., "*De Novo Protein Design: Fully Automated Sequence Selection*", Science 1997, 278 (5335):82-87.
Flicek et al., "*Sense From Sequence Reads: Methods for Alignment and Assembly*" Nature Methods Supplement Oct. 15, 2009, 6(11S):S6-S12.
Gonnet et al., "*Exhaustive Matching of the Entire Protein Sequence Database*", Science 1992, 256(5062):1443-1445.

(Continued)

*Primary Examiner* — Anna Skibinsky
(74) *Attorney, Agent, or Firm* — Kilpatrick Townsend & Stockton LLP

(57) ABSTRACT

Generating an index includes receiving a reference sequence and applying one or more key patterns to the reference sequence to obtain a plurality of keys in the index. Each of the one or more key patterns is derived based on a corresponding set of oligomer sequence relationships of a plurality of oligomer sequences that are expected to be generated from the reference, and the keys correspond to a plurality of candidate and/or validated locations in the reference sequence.

28 Claims, 15 Drawing Sheets

(56) References Cited

OTHER PUBLICATIONS

Han al el., "*SPIDER: Software for Protein Identification From Sequence Tags With De Novo Sequencing Error*", 2004 IEEE Computational Systems Bioinformatics Conference 2004. (Retrieved from the Internet on Nov. 1, 2010: <URL: http://citeseerx.ist.psu.edu/viewdoc/download?doi=10.1.1.71.8935&rep=rep1&type=pdf>) p. 1-18.

Margulies et al, "*Genome Sequencing in Microfabricated High-Density Picolitre Reactors*", Nature 2005, 437:376-380.

Ning at al., "*SSAHA: A Fast Search Method for Large DNA Databases*", pp. 1725-1729, Genome Research 2001,11(10):1725-1729.

Pevzner et al. "*An Eulerian Path Approach to DNA Fragment Assembly*", Proceedings of the National Academy of Sciences 2001, 98(17):9748-9753.

Ronaghi et al., "*Real-Time DNA Sequencing Using Detection of Pyrophosphate Release*", Anal. Biochem, 1996, 242:84-89.

Webb et al. "*BALSA: Bayesian Algorithm for Local Sequence Alignment*" Nucleic Acids Research 2002, 30(5):1268-1277; p. 1269-1272.

Zerbino et al. "*Velvet: Algorithms for De Novo Short Read Assembly Using De Bruijn Graphs*", Genome Research 2008, 18(5):821-829; p. 821-822, 825.

PCT International Search Report and Written Opinion of the International Searching Authority, issued Jun. 23, 2010, application No. PCT/US2010/022912.

Jiang, Hui, et al., "SeqMap: mapping massive amount of oligonucleotides to the genome," Bioinformatics, 2008, vol. 24, No. 20, pp. 2395-2396.

Li, Ruiqiang, et al., "SOAP: short oligonucleotide alignment program," Bioinformatics, 2008, vol. 24, No. 5, pp. 713-714.

Li, Heng, et al., "Mapping short DNA sequencing reads and calling variants using mapping quality scores," Genome Research, Aug. 19, 2008, pp. 1851-1858.

European Search Report mailed Dec. 9, 2013 in European Patent Application No. 10739024.7, 10 pages.

\* cited by examiner

| Key | Location |
|---|---|
| AAAAAA AAAAAA AAAA | Chr2: 10991917 |
| AAAAAA AAAAAA AAAA | Chr7:4534161 |
| AAAAAA AAAAAA AAAC | Chr5: 1121222 |
| AAAAAA AAAAAA AAAG | Chr3: 4352556 |
| ... | ... |
| TCTAGCCATGTGGAA | Chr1: 5312526 |
| ... | ... |
| TTTTAGCCGTGTGGCA | Chr1: 5312525 |

SEQUENCE LISTING

<160> NUMBER OF SEQ ID NOS: 98

<210> SEQ ID NO 1
<211> LENGTH: 32
<212> TYPE: DNA
<213> ORGANISM: Homo sapiens

<400> SEQUENCE: 1
tgctattcat tagccaagtg tgggtcaagg ta                              32

<210> SEQ ID NO 2
<211> LENGTH: 20
<212> TYPE: DNA
<213> ORGANISM: HOMO SAPIENS

<400> SEQUENCE: 2
ttcattagcc gtgtgggtca                                            20

<210> SEQ ID NO 3
<211> LENGTH: 20
<212> TYPE: DNA
<213> ORGANISM: HOMO SAPIENS

<400> SEQUENCE: 3
ttagccgtgt ggttcacagt                                            20

<210> SEQ ID NO 4
<211> LENGTH: 14
<212> TYPE: DNA
<213> ORGANISM: HOMO SAPIENS

<400> SEQUENCE: 4
tttagccgtg tgga                                                  14

<210> SEQ ID NO 5
<211> LENGTH: 16
<212> TYPE: DNA
<213> ORGANISM: HOMO SAPIENS
<220> FEATURE:
<221> NAME/KEY: misc_feature
<222> LOCATION: (2)..(2)
<223> OTHER INFORMATION: n = a, c, g or t

<400> SEQUENCE: 5
tnttagccgt gtggca                                                16

<210> SEQ ID NO 6
<211> LENGTH: 16
<212> TYPE: DNA
<213> ORGANISM: Homo sapiens

<400> SEQUENCE: 6
ttttagccgt gtggca                                                16

<210> SEQ ID NO 7
<211> LENGTH: 16
<212> TYPE: DNA
<213> ORGANISM: HOMO SAPIENS

<400> SEQUENCE: 7
tattagccgt gtggca                                                16

<210> SEQ ID NO 8

```
<211> LENGTH: 16
<212> TYPE: DNA
<213> ORGANISM: HOMO SAPIENS
<220> FEATURE:
<221> NAME/KEY: misc_feature
<222> LOCATION: (14)..(14)
<223> OTHER INFORMATION: w = a or t

<400> SEQUENCE: 8
ttagccgtgt ggtwca                                                       16

<210> SEQ ID NO 9
<211> LENGTH: 16
<212> TYPE: DNA
<213> ORGANISM: HOMO SAPIENS

<400> SEQUENCE: 9
ttagccgtgt ggttca                                                       16

<210> SEQ ID NO 10
<211> LENGTH: 16
<212> TYPE: DNA
<213> ORGANISM: HOMO SAPIENS

<400> SEQUENCE: 10
ttagccgtgt ggtaca                                                       16

<210> SEQ ID NO 11
<211> LENGTH: 16
<212> TYPE: DNA
<213> ORGANISM: HOMO SAPIENS
<220> FEATURE:
<221> NAME/KEY: misc_feature
<222> LOCATION: (2)..(2)
<223> OTHER INFORMATION: w = a or t

<400> SEQUENCE: 11
twttagccgt gtggca                                                       16

<210> SEQ ID NO 12
<211> LENGTH: 16
<212> TYPE: DNA
<213> ORGANISM: HOMO SAPIENS

<400> SEQUENCE: 12
tgttagccgt gtggca                                                       16

<210> SEQ ID NO 13
<211> LENGTH: 16
<212> TYPE: DNA
<213> ORGANISM: HOMO SAPIENS

<400> SEQUENCE: 13
tattagccgt gtggca                                                       16

<210> SEQ ID NO 14
<211> LENGTH: 16
<212> TYPE: DNA
<213> ORGANISM: HOMO SAPIENS

<400> SEQUENCE: 14
ttttagccgt gtggca                                                       16

<210> SEQ ID NO 15
<211> LENGTH: 16
<212> TYPE: DNA
```

```
<213> ORGANISM: HOMO SAPIENS

<400> SEQUENCE: 15
tcttagccgt gtggca                                                   16

<210> SEQ ID NO 16
<211> LENGTH: 16
<212> TYPE: DNA
<213> ORGANISM: HOMO SAPIENS
<220> FEATURE:
<221> NAME/KEY: misc_feature
<222> LOCATION: (14)..(14)
<223> OTHER INFORMATION: n is a, c, g, or t

<400> SEQUENCE: 16
ttagccgtgt ggtnca                                                   16

<210> SEQ ID NO 17
<211> LENGTH: 16
<212> TYPE: DNA
<213> ORGANISM: HOMO SAPIENS

<400> SEQUENCE: 17
ttagccgtgt ggtgca                                                   16

<210> SEQ ID NO 18
<211> LENGTH: 16
<212> TYPE: DNA
<213> ORGANISM: HOMO SAPIENS

<400> SEQUENCE: 18
ttagccgtgt ggtaca                                                   16

<210> SEQ ID NO 19
<211> LENGTH: 16
<212> TYPE: DNA
<213> ORGANISM: HOMO SAPIENS

<400> SEQUENCE: 19
ttagccgtgt ggttca                                                   16

<210> SEQ ID NO 20
<211> LENGTH: 16
<212> TYPE: DNA
<213> ORGANISM: HOMO SAPIENS

<400> SEQUENCE: 20
ttagccgtgt ggtcca                                                   16

<210> SEQ ID NO 21
<211> LENGTH: 20
<212> TYPE: DNA
<213> ORGANISM: HOMO SAPIENS
<220> FEATURE:
<221> NAME/KEY: misc_feature
<222> LOCATION: (4)..(4)
<223> OTHER INFORMATION: n = a, c, g or t
<220> FEATURE:
<221> NAME/KEY: misc_feature
<222> LOCATION: (17)..(17)
<223> OTHER INFORMATION: n = a, c, g or t

<400> SEQUENCE: 21
ttcnttagcc gtgtggntca                                               20

<210> SEQ ID NO 22
```

```
<211> LENGTH: 20
<212> TYPE: DNA
<213> ORGANISM: HOMO SAPIENS
<220> FEATURE:
<221> NAME/KEY: misc_feature
<222> LOCATION: (16)..(17)
<223> OTHER INFORMATION: n = a, c, g or t

<400> SEQUENCE: 22
ttagccgtgt ggttcnntca                                              20

<210> SEQ ID NO 23
<211> LENGTH: 20
<212> TYPE: DNA
<213> ORGANISM: HOMO SAPIENS

<400> SEQUENCE: 23
ttcgttagcc gtgtgggtca                                              20

<210> SEQ ID NO 24
<211> LENGTH: 20
<212> TYPE: DNA
<213> ORGANISM: HOMO SAPIENS

<400> SEQUENCE: 24
ttcgttagcc gtgtggatca                                              20

<210> SEQ ID NO 25
<211> LENGTH: 20
<212> TYPE: DNA
<213> ORGANISM: HOMO SAPIENS

<400> SEQUENCE: 25
ttcgttagcc gtgtggttca                                              20

<210> SEQ ID NO 26
<211> LENGTH: 20
<212> TYPE: DNA
<213> ORGANISM: HOMO SAPIENS

<400> SEQUENCE: 26
ttcgttagcc gtgtggctca                                              20

<210> SEQ ID NO 27
<211> LENGTH: 20
<212> TYPE: DNA
<213> ORGANISM: HOMO SAPIENS

<400> SEQUENCE: 27
ttcattagcc gtgtgggtca                                              20

<210> SEQ ID NO 28
<211> LENGTH: 20
<212> TYPE: DNA
<213> ORGANISM: HOMO SAPIENS

<400> SEQUENCE: 28
ttcattagcc gtgtggatca                                              20

<210> SEQ ID NO 29
<211> LENGTH: 20
<212> TYPE: DNA
<213> ORGANISM: HOMO SAPIENS

<400> SEQUENCE: 29
```
ttcattagcc gtgtggttca        20

<210> SEQ ID NO 30
<211> LENGTH: 20
<212> TYPE: DNA
<213> ORGANISM: HOMO SAPIENS

<400> SEQUENCE: 30
ttcattagcc gtgtggctca        20

<210> SEQ ID NO 31
<211> LENGTH: 20
<212> TYPE: DNA
<213> ORGANISM: HOMO SAPIENS

<400> SEQUENCE: 31
ttctttagcc gtgtgggtca        20

<210> SEQ ID NO 32
<211> LENGTH: 20
<212> TYPE: DNA
<213> ORGANISM: HOMO SAPIENS

<400> SEQUENCE: 32
ttctttagcc gtgtggatca        20

<210> SEQ ID NO 33
<211> LENGTH: 20
<212> TYPE: DNA
<213> ORGANISM: HOMO SAPIENS

<400> SEQUENCE: 33
ttctttagcc gtgtggttca        20

<210> SEQ ID NO 34
<211> LENGTH: 20
<212> TYPE: DNA
<213> ORGANISM: HOMO SAPIENS

<400> SEQUENCE: 34
ttctttagcc gtgtggctca        20

<210> SEQ ID NO 35
<211> LENGTH: 20
<212> TYPE: DNA
<213> ORGANISM: HOMO SAPIENS

<400> SEQUENCE: 35
ttccttagcc gtgtgggtca        20

<210> SEQ ID NO 36
<211> LENGTH: 20
<212> TYPE: DNA
<213> ORGANISM: HOMO SAPIENS

<400> SEQUENCE: 36
ttccttagcc gtgtggatca        20

<210> SEQ ID NO 37
<211> LENGTH: 20
<212> TYPE: DNA
<213> ORGANISM: HOMO SAPIENS

<400> SEQUENCE: 37
ttccttagcc gtgtggttca                                                        20

<210> SEQ ID NO 38
<211> LENGTH: 20
<212> TYPE: DNA
<213> ORGANISM: HOMO SAPIENS

<400> SEQUENCE: 38
ttccttagcc gtgtggctca                                                        20

<210> SEQ ID NO 39
<211> LENGTH: 20
<212> TYPE: DNA
<213> ORGANISM: HOMO SAPIENS

<400> SEQUENCE: 39
ttggttagcc gtgtgggtca                                                        20

<210> SEQ ID NO 40
<211> LENGTH: 20
<212> TYPE: DNA
<213> ORGANISM: HOMO SAPIENS

<400> SEQUENCE: 40
ttggttagcc gtgtggatca                                                        20

<210> SEQ ID NO 41
<211> LENGTH: 20
<212> TYPE: DNA
<213> ORGANISM: HOMO SAPIENS

<400> SEQUENCE: 41
ttggttagcc gtgtggttca                                                        20

<210> SEQ ID NO 42
<211> LENGTH: 20
<212> TYPE: DNA
<213> ORGANISM: HOMO SAPIENS

<400> SEQUENCE: 42
ttggttagcc gtgtggctca                                                        20

<210> SEQ ID NO 43
<211> LENGTH: 20
<212> TYPE: DNA
<213> ORGANISM: HOMO SAPIENS

<400> SEQUENCE: 43
ttgattagcc gtgtgggtca                                                        20

<210> SEQ ID NO 44
<211> LENGTH: 20
<212> TYPE: DNA
<213> ORGANISM: HOMO SAPIENS

<400> SEQUENCE: 44
ttgattagcc gtgtggatca                                                        20

<210> SEQ ID NO 45
<211> LENGTH: 20
<212> TYPE: DNA
<213> ORGANISM: HOMO SAPIENS

<400> SEQUENCE: 45
ttgattagcc gtgtggttca                                                    20

<210> SEQ ID NO 46
<211> LENGTH: 20
<212> TYPE: DNA
<213> ORGANISM: HOMO SAPIENS

<400> SEQUENCE: 46
ttgattagcc gtgtggctca                                                    20

<210> SEQ ID NO 47
<211> LENGTH: 20
<212> TYPE: DNA
<213> ORGANISM: HOMO SAPIENS

<400> SEQUENCE: 47
ttgcttagcc gtgtgggtca                                                    20

<210> SEQ ID NO 48
<211> LENGTH: 20
<212> TYPE: DNA
<213> ORGANISM: HOMO SAPIENS

<400> SEQUENCE: 48
ttgcttagcc gtgtggatca                                                    20

<210> SEQ ID NO 49
<211> LENGTH: 20
<212> TYPE: DNA
<213> ORGANISM: HOMO SAPIENS

<400> SEQUENCE: 49
ttgcttagcc gtgtggttca                                                    20

<210> SEQ ID NO 50
<211> LENGTH: 20
<212> TYPE: DNA
<213> ORGANISM: HOMO SAPIENS

<400> SEQUENCE: 50
ttgcttagcc gtgtggctca                                                    20

<210> SEQ ID NO 51
<211> LENGTH: 20
<212> TYPE: DNA
<213> ORGANISM: HOMO SAPIENS

<400> SEQUENCE: 51
ttagttagcc gtgtgggtca                                                    20

<210> SEQ ID NO 52
<211> LENGTH: 20
<212> TYPE: DNA
<213> ORGANISM: HOMO SAPIENS

<400> SEQUENCE: 52
ttagttagcc gtgtggatca                                                    20

<210> SEQ ID NO 53
<211> LENGTH: 20
<212> TYPE: DNA
<213> ORGANISM: HOMO SAPIENS

<400> SEQUENCE: 53
ttagttagcc gtgtggttca                                                    20

<210> SEQ ID NO 54
<211> LENGTH: 20
<212> TYPE: DNA
<213> ORGANISM: HOMO SAPIENS

<400> SEQUENCE: 54
ttagttagcc gtgtggctca                                                    20

<210> SEQ ID NO 55
<211> LENGTH: 20
<212> TYPE: DNA
<213> ORGANISM: HOMO SAPIENS

<400> SEQUENCE: 55
ttaattagcc gtgtgggtca                                                    20

<210> SEQ ID NO 56
<211> LENGTH: 20
<212> TYPE: DNA
<213> ORGANISM: HOMO SAPIENS

<400> SEQUENCE: 56
ttaattagcc gtgtggatca                                                    20

<210> SEQ ID NO 57
<211> LENGTH: 20
<212> TYPE: DNA
<213> ORGANISM: HOMO SAPIENS

<400> SEQUENCE: 57
ttaattagcc gtgtggttca                                                    20

<210> SEQ ID NO 58
<211> LENGTH: 20
<212> TYPE: DNA
<213> ORGANISM: HOMO SAPIENS

<400> SEQUENCE: 58
ttaattagcc gtgtggctca                                                    20

<210> SEQ ID NO 59
<211> LENGTH: 20
<212> TYPE: DNA
<213> ORGANISM: HOMO SAPIENS

<400> SEQUENCE: 59
ttatttagcc gtgtgggtca                                                    20

<210> SEQ ID NO 60
<211> LENGTH: 20
<212> TYPE: DNA
<213> ORGANISM: HOMO SAPIENS

<400> SEQUENCE: 60
ttatttagcc gtgtggatca                                                    20

<210> SEQ ID NO 61
<211> LENGTH: 20
<212> TYPE: DNA
<213> ORGANISM: HOMO SAPIENS

<400> SEQUENCE: 61
ttatttagcc gtgtggttca                                           20

<210> SEQ ID NO 62
<211> LENGTH: 20
<212> TYPE: DNA
<213> ORGANISM: HOMO SAPIENS

<400> SEQUENCE: 62
ttatttagcc gtgtggctca                                           20

<210> SEQ ID NO 63
<211> LENGTH: 20
<212> TYPE: DNA
<213> ORGANISM: HOMO SAPIENS

<400> SEQUENCE: 63
ttacttagcc gtgtgggtca                                           20

<210> SEQ ID NO 64
<211> LENGTH: 20
<212> TYPE: DNA
<213> ORGANISM: HOMO SAPIENS

<400> SEQUENCE: 64
ttacttagcc gtgtggatca                                           20

<210> SEQ ID NO 65
<211> LENGTH: 20
<212> TYPE: DNA
<213> ORGANISM: HOMO SAPIENS

<400> SEQUENCE: 65
ttacttagcc gtgtggttca                                           20

<210> SEQ ID NO 66
<211> LENGTH: 20
<212> TYPE: DNA
<213> ORGANISM: HOMO SAPIENS

<400> SEQUENCE: 66
ttacttagcc gtgtggctca                                           20

<210> SEQ ID NO 67
<211> LENGTH: 20
<212> TYPE: DNA
<213> ORGANISM: HOMO SAPIENS

<400> SEQUENCE: 67
tttgttagcc gtgtgggtca                                           20

<210> SEQ ID NO 68
<211> LENGTH: 20
<212> TYPE: DNA
<213> ORGANISM: HOMO SAPIENS

<400> SEQUENCE: 68
tttgttagcc gtgtggatca                                           20

<210> SEQ ID NO 69
<211> LENGTH: 20
<212> TYPE: DNA
<213> ORGANISM: HOMO SAPIENS

<400> SEQUENCE: 69

```
tttgttagcc gtgtggttca                                              20

<210> SEQ ID NO 70
<211> LENGTH: 20
<212> TYPE: DNA
<213> ORGANISM: HOMO SAPIENS

<400> SEQUENCE: 70
tttgttagcc gtgtggctca                                              20

<210> SEQ ID NO 71
<211> LENGTH: 20
<212> TYPE: DNA
<213> ORGANISM: HOMO SAPIENS

<400> SEQUENCE: 71
tttattagcc gtgtgggtca                                              20

<210> SEQ ID NO 72
<211> LENGTH: 20
<212> TYPE: DNA
<213> ORGANISM: HOMO SAPIENS

<400> SEQUENCE: 72
tttattagcc gtgtggatca                                              20

<210> SEQ ID NO 73
<211> LENGTH: 20
<212> TYPE: DNA
<213> ORGANISM: HOMO SAPIENS

<400> SEQUENCE: 73
tttattagcc gtgtggttca                                              20

<210> SEQ ID NO 74
<211> LENGTH: 20
<212> TYPE: DNA
<213> ORGANISM: HOMO SAPIENS

<400> SEQUENCE: 74
tttattagcc gtgtggctca                                              20

<210> SEQ ID NO 75
<211> LENGTH: 20
<212> TYPE: DNA
<213> ORGANISM: HOMO SAPIENS

<400> SEQUENCE: 75 tttttagcc gtgtgggtca                                               20

<210> SEQ ID NO 76
<211> LENGTH: 20
<212> TYPE: DNA
<213> ORGANISM: HOMO SAPIENS

<400> SEQUENCE: 76 tttttagcc gtgtggatca                                               20

<210> SEQ ID NO 77
<211> LENGTH: 20
<212> TYPE: DNA
<213> ORGANISM: HOMO SAPIENS

<400> SEQUENCE: 77
```

```
tttttttagcc gtgtggttca                                              20

<210> SEQ ID NO 78
<211> LENGTH: 20
<212> TYPE: DNA
<213> ORGANISM: HOMO SAPIENS

<400> SEQUENCE: 78 tttttttagcc gtgtggctca                                              20

<210> SEQ ID NO 79
<211> LENGTH: 20
<212> TYPE: DNA
<213> ORGANISM: HOMO SAPIENS

<400> SEQUENCE: 79
tttcttagcc gtgtgggtca                                               20

<210> SEQ ID NO 80
<211> LENGTH: 20
<212> TYPE: DNA
<213> ORGANISM: HOMO SAPIENS

<400> SEQUENCE: 80
tttcttagcc gtgtggatca                                               20

<210> SEQ ID NO 81
<211> LENGTH: 20
<212> TYPE: DNA
<213> ORGANISM: HOMO SAPIENS

<400> SEQUENCE: 81
tttcttagcc gtgtggttca                                               20

<210> SEQ ID NO 82
<211> LENGTH: 20
<212> TYPE: DNA
<213> ORGANISM: HOMO SAPIENS

<400> SEQUENCE: 82
tttcttagcc gtgtggctca                                               20

<210> SEQ ID NO 83
<211> LENGTH: 20
<212> TYPE: DNA
<213> ORGANISM: HOMO SAPIENS

<400> SEQUENCE: 83
ttcgttagcc gtgtgggtca                                               20

<210> SEQ ID NO 84
<211> LENGTH: 20
<212> TYPE: DNA
<213> ORGANISM: HOMO SAPIENS

<400> SEQUENCE: 84
ttcgttagcc gtgtggatca                                               20

<210> SEQ ID NO 85
<211> LENGTH: 20
<212> TYPE: DNA
<213> ORGANISM: HOMO SAPIENS

<400> SEQUENCE: 85
```

```
ttcgttagcc gtgtggttca                                              20

<210> SEQ ID NO 86
<211> LENGTH: 20
<212> TYPE: DNA
<213> ORGANISM: HOMO SAPIENS

<400> SEQUENCE: 86
ttcgttagcc gtgtggctca                                              20

<210> SEQ ID NO 87
<211> LENGTH: 20
<212> TYPE: DNA
<213> ORGANISM: HOMO SAPIENS

<400> SEQUENCE: 87
ttcattagcc gtgtgggtca                                              20

<210> SEQ ID NO 88
<211> LENGTH: 20
<212> TYPE: DNA
<213> ORGANISM: HOMO SAPIENS

<400> SEQUENCE: 88
ttcattagcc gtgtggatca                                              20

<210> SEQ ID NO 89
<211> LENGTH: 20
<212> TYPE: DNA
<213> ORGANISM: HOMO SAPIENS

<400> SEQUENCE: 89
ttcattagcc gtgtggttca                                              20

<210> SEQ ID NO 90
<211> LENGTH: 20
<212> TYPE: DNA
<213> ORGANISM: HOMO SAPIENS

<400> SEQUENCE: 90
ttcattagcc gtgtggctca                                              20

<210> SEQ ID NO 91
<211> LENGTH: 20
<212> TYPE: DNA
<213> ORGANISM: HOMO SAPIENS

<400> SEQUENCE: 91
ttctttagcc gtgtgggtca                                              20

<210> SEQ ID NO 92
<211> LENGTH: 20
<212> TYPE: DNA
<213> ORGANISM: HOMO SAPIENS

<400> SEQUENCE: 92
ttctttagcc gtgtggatca                                              20

<210> SEQ ID NO 93
<211> LENGTH: 20
<212> TYPE: DNA
<213> ORGANISM: HOMO SAPIENS

<400> SEQUENCE: 93
```

-continued

```
ttctttagcc gtgtggttca                                          20

<210> SEQ ID NO 94
<211> LENGTH: 20
<212> TYPE: DNA
<213> ORGANISM: HOMO SAPIENS

<400> SEQUENCE: 94
ttctttagcc gtgtggctca                                          20

<210> SEQ ID NO 95
<211> LENGTH: 20
<212> TYPE: DNA
<213> ORGANISM: HOMO SAPIENS

<400> SEQUENCE: 95
ttccttagcc gtgtgggtca                                          20

<210> SEQ ID NO 96
<211> LENGTH: 20
<212> TYPE: DNA
<213> ORGANISM: HOMO SAPIENS

<400> SEQUENCE: 96
ttccttagcc gtgtggatca                                          20

<210> SEQ ID NO 97
<211> LENGTH: 20
<212> TYPE: DNA
<213> ORGANISM: HOMO SAPIENS

<400> SEQUENCE: 97
ttccttagcc gtgtggttca                                          20

<210> SEQ ID NO 98
<211> LENGTH: 20
<212> TYPE: DNA
<213> ORGANISM: HOMO SAPIENS

<400> SEQUENCE: 98
ttccttagcc gtgtggctca                                          20
```

| ... | ... |

INDEXING A REFERENCE SEQUENCE FOR OLIGOMER SEQUENCE MAPPING

CROSS-REFERENCE TO RELATED APPLICATIONS

This application claims priority to provisional application Ser. No. 61/149,665 filed Feb. 3, 2009, which is hereby incorporated by reference in its entirety

BACKGROUND OF THE INVENTION

Genetic studies have seen rapid advances in recent years. The entire genomes of specific organisms, including some individual human beings, have been sequenced and become available as references. In genetic research, genetic testing, personalized medicine, and many other applications, it is often useful to obtain a sample of genetic material, determine a sequence of that sample, and to map that sample sequence to a location on an available reference. Once the mapping is done, a comparison can be made to a reference in order to identify polymorphisms or mutations or obtain other useful information.

Existing approaches typically map long, contiguous sample sequences to locations in a reference. However, some techniques used for obtaining sample sequences yield data sets comprising short sequences (sometimes referred to as oligomers) with predicted spatial relationships. Such 'polyoligomer data sets' consist of multiple oligomers that have variable but constrained amounts of spacing or overlap (referred to as separation distance) between oligomers. Where individual oligomers are too short to identify one or a small number of possible locations on a reference sequence, and the spacing between oligomers is variable, existing approaches are not adequate.

It would be useful to have indexes with the ability to accurately map relatively short oligomer sequences with variable separation distances to a reference. It would also be desirable to create indexes that would allow such mapping to be efficient both in terms of computational speed and cost

SUMMARY OF THE INVENTION

The present invention provides methods of producing searchable indexes for analysis of polyoligomer data sets. The indexes are created by generating keys from a reference corresponding to predicted sequence relationships within the data sets. The index keys are generated using key patterns that correspond to predicted data sets based on the reference. The index allows external data sets to be mapped via keys within the index via the use of keys generated from the data sets; mapping of the keys to the index allows identification of potential locations of the data set within the reference.

In one implementation, the invention provides a method of generating an index comprising application of one or more key patterns to a reference to generate a plurality of keys. Such key patterns are based on predicted reference data sets having at least one variable separation distance. The keys are provided in a searchable medium, and are preferably stored in a computer readable medium.

In another implementation, the invention provides a system for generating an index for oligomer sequence analysis, comprising an interface configured to receive a reference, and a processor coupled to the interface, with the processor configured to apply one or more key patterns to the reference to obtain a plurality of keys in the index. Each of the key patterns is derived from predicted sequence relationships of data sets, and each data set has at least one area of variable separation distance. The plurality of keys in the index corresponds to a plurality of possible locations in the reference.

In yet another implementation, the invention provides a computer program product for generating an index, the computer program product being embodied in a computer readable medium and comprising computer instructions for receiving a reference and applying one or more key patterns to the reference to obtain a plurality of keys in an index. The key patterns are derived from predicted data sets based on the reference, and each data set has at least one area of variable separation distance. The plurality of keys in the index corresponds to a plurality of possible locations in the reference.

BRIEF DESCRIPTION OF THE DRAWINGS

Various implementations of the invention are disclosed in the following detailed description and the accompanying drawings. These are for exemplary purposes only, and not intended to limit the scope of the invention, which shall only be limited by the claims.

FIG. 4A is a schematic illustration of an index.

FIGS. 8A-8D are diagrams illustrating examples of keys generation using key patterns and substitutions or deletion of ambiguous positions.

DETAILED DESCRIPTION

Figure 1A:
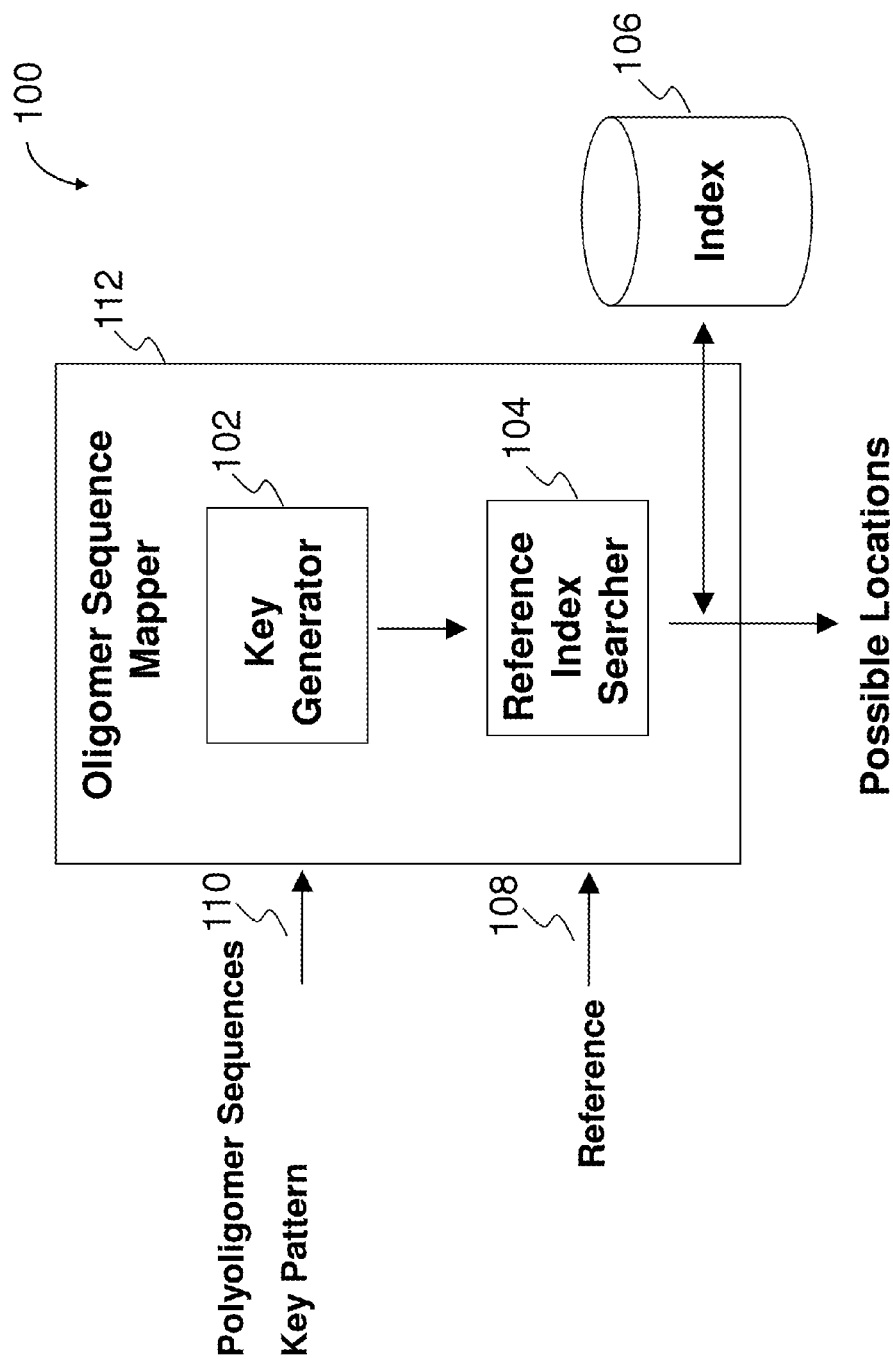
FIG. 1A is a block diagram illustrating an implementation of a system for mapping oligomer sequences.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term "processor" refers to one or more devices, circuits, and/ or processing cores configured to process data, such as computer program instructions.

A detailed description of one or more embodiments of the invention is provided below along with accompanying figures that illustrate the principles of the invention. The invention is described in connection with such embodiments, but the invention is not limited to any implementation. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Definitions

The term "polyoligomer data set" (also, simply "polyoligomer" or "data set") refers to a collection of two or more determined oligomer sequences (e.g. using a biochemical process), and whose separations from one another are, or for computational purposes are assumed to be, restricted to certain known or estimated values.

The term "reference" refers to a known sequence of nucleotides. It may be an entire genome sequence of a reference organism, a portion of a reference genome, a consensus sequence of many reference organisms, a compilation sequence based on different components of different organisms, or any other appropriate sequence. It may also include information regarding variations of the reference known to be found in a population of organisms.

The term "reference index" refers to an index relating keys consisting of sequences of bases to locations in the reference that is created by application of one or more key patterns to a reference.

The term "sequence relationship" refers to a known, inferred or hypothesized specification of separation distances among two or more oligomers, e.g. defined as the number of (unknown) bases between two oligomers. The sequence relationship may be a separation distance, an overlap distance, or the two oligos may be directly adjacent to one another in the reference.

The term "instantiation" refers to the derivation of a sequence of contiguous bases, some known, some possibly unknown, by applying a specific set of sequence relationships to a polyoligomer data set. The term may also refer to the derived sequence itself, which may otherwise be called an "instantiated polyoligomer".

The term "mapping" refers to a process which relates a polyoligomer to zero, one or more locations in the reference to which the polyoligomer is similar, e.g., by matching the instantiated polyoligomer to one or more keys within an index of the invention corresponding to a location within a reference.

The term "candidate locations" refers to potential locations in a reference of oligomers of a data set identified based on the generation of keys from the data set and the mapping of these keys using a reference index. Since a key derived from a given polyoligomer does not necessarily include all bases of the polyoligomer, the polyoligomer may or may not be a perfect match with a given candidate location in a reference.

The phrase "perfect match" means an exact data match between one possible instantiation and the reference. In certain implementations, an unknown base in a data set may be considered to be a perfect match to any base.

The term "validated locations" means candidate locations which have been further confirmed to be locations within a reference that are compatible with a polyoligomer.

The phrase "degree of conservation" as used herein refers to the likelihood that one or more of the bases in the oligomer sequences of a data set will be in a given position in the key when the key pattern is applied to the correct instantiation of the data set.

The term "sample analysis" means any use of the information obtained through use of the keys and indexes of the invention, including but not limited to genomic analysis (including sequence assembly), polymorphism analysis, mutation analysis, phylogenetic analysis and the like.

The term "key pattern" refers to a predetermined spatial relationship that is used to derive one or more keys from a reference and/or an instantiated polyoligomer.

The Invention in General

Mapping of polyoligomer data sets to locations in a reference is disclosed. The oligomer sequences are obtained from a sample of genetic material (such as DNA or RNA molecules from an organism), e.g., by subjecting the sample or a fragment thereof to a biochemical process. The oligomer sequences are mapped to one or more possible locations in a reference and those locations are output to facilitate further sample analysis.

In some embodiments, an index is generated for mapping key sequences to locations in the reference. The key sequences in the index are generated based on the reference and key patterns that are derived from expected oligomer sequence relationships. Examples of such oligomer sequence relationships include oligomer sequence length, the likely amount of spacing or overlap between oligomer sequences (also referred to as "separation distance"), the statistical distribution of these separation distances (the "distance variations"), and the statistical distribution of possible combinations of distance variations for sets of related oligomer sequences. The relationships may be determined based on existing knowledge about the biochemical process used to generate the oligomer sequences (i.e., based on oligomer sequences that would be expected to be obtained if the biochemical process were applied to a sample), empirical estimates based on preliminary analysis of oligomer sequences, estimation by experts, or other appropriate techniques.

The oligomer sequence relationships depend at least in part on the biochemical process used to generate the oligomers. Numerous processes can be used to generate oligomer data sets for use with the present invention. These include, but are not limited to hybridization methods as disclosed in U.S. Pat. Nos. 6,864,052; 6,309,824; 6,401,267; sequencing-by-synthesis methods as disclosed in U.S. Pat. Nos. 6,210,891; 6,828,100, 6,833,246; 6,911,345; 7,329,496 and Margulies, et al. (2005), *Nature* 437:376-380 and Ronaghi, et al. (1996), *Anal. Biochem.* 242:84-89; ligation-based methods as disclosed in U.S. Pat. No. 6,306,597, WO2006073504, WO2007120208, all of which are incorporated by reference in their entirety. In a specific implementation, a Combinatorial Probe Anchor Ligation (cPAL) process is used in some embodiments (see U.S. Ser. No. 11/679,124, filed Feb. 24, 2007, which is incorporated herein by reference in its entirety).

The processes used to generate related oligomers in data sets may result in oligomers of various sizes, including different sizes within single data sets. For purposes of example only, and not to be limiting in scope, the oligomer sequences discussed in detail below for purposes of illustration are described as having a length of 6 bases, and a distance variation of +/−2 or +/−3 bases. It will be apparent to one skilled in the art upon reading the present disclosure that other sequence lengths and distance variations (e.g., +/−1 or +/−4) can be used in the described implementations.

The key generator also receives as one of its inputs one or more key patterns. The key patterns are derived from one or more oligomer sequence relationships. In some embodiments, various key patterns for different oligomer relationships are derived prior to the mapping process, stored, and retrieved as needed.

FIG. 1A is a block diagram illustrating an implementation of a system for mapping oligomer sequences onto a reference. In this example, the system 100 includes a communication interface 110 configured to receive inputs. Examples of a communication interface include without limitation external connections, such as a port, cable, wire line or wireless network interface card, etc., and internal connections such as a communication bus. The interface 110 is coupled to an oligomer sequence mapper component 112, which includes a key generator 102 and a reference index search engine 104. The key generator receives as one of its inputs a set of related oligomer sequences, e.g., a polyoligomer data set, and receives as another of its inputs one or more key patterns. When mapped to the reference, the related oligomer sequences are expected to be located with respect to each other within a small range of expected separation distance. The oligomer sequence relationships may include the separation distance or other relationships or expected correlations between oligomers.

Based on its inputs, the key generator generates one or more keys, which are strings of base sequences, compressed representations of base sequences or any other appropriate representations of base sequences that are suitable for computer processing. Using the keys, a reference index search engine 104 queries an index 106 to determine possible locations of the oligomer sequences in a reference 108. In the examples discussed below, keys within index 106 include strings that are permutations of bases. The index maps keys to their respective possible locations in the reference. These candidate locations are then examined to confirm the match between a data set and a given location, by comparison to the reference 108. The validated locations may be output and used for further sample analysis, which can have applications in genetic research, genetic testing, personalized medicine including diagnosis, prognosis and identification of predispositions, and the like.

An oligomer sequence mapper 112 with key generator 102, reference search engine 104, and index 106 are shown as separate logical components in the diagram. In some embodiments the components are separate components such as separate processors or separate processes operating on one processor, and in some embodiments some of the components may be combined and implemented on the same device, as a single integrated circuit, and/or as parts in the same process operating on a processor.

Figure 1B:
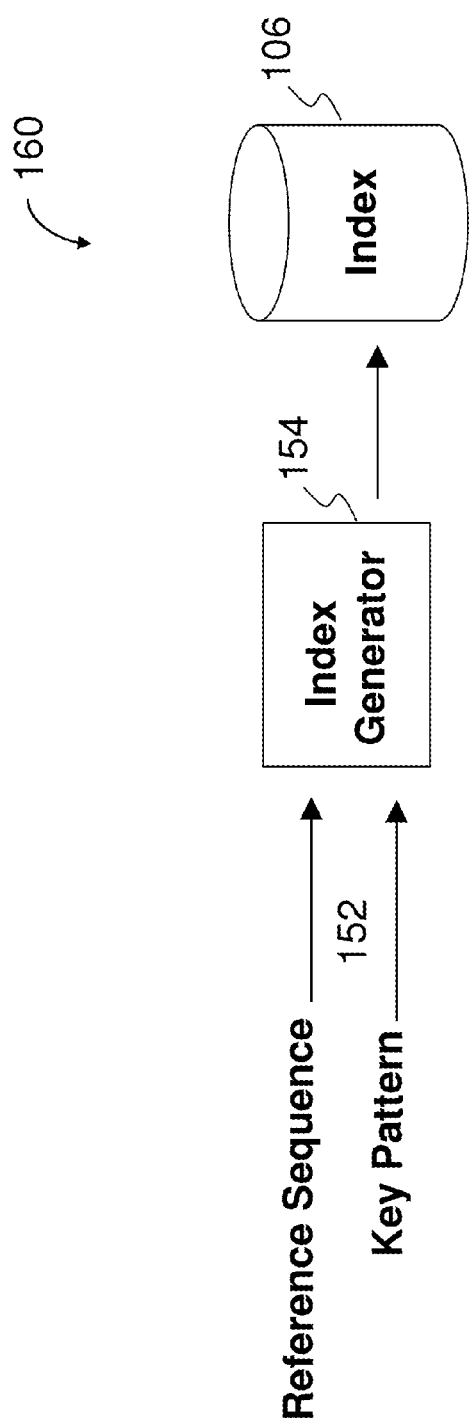
FIG. 1B is a block diagram illustrating an implementation of a system for generating an index.

FIG. 1B is a block diagram illustrating an implementation of a system for generating an index. System 160 may also include a general purpose computer and/or specialized hardware. In this example, system 160 includes an interface 152, which is configured to receive inputs such as the reference and one or more key patterns. The interface is coupled to an index generator 154 that includes a processor configured to generate keys based on the inputs. Keys and the locations from which they are derived are maintained in index 106, which may be stored on a computer readable storage medium such as a computer data storage device (e.g., random access memory), disk storage, and/or any other appropriate storage device. Such storage devices are optionally coupled with a central processing unit.

The keys for a specific data set are generated by applying pre-defined key patterns to the data set, and the obtained keys can then be compared to keys within a reference index. In certain implementations, the key patterns are applied directly to the data set without any further manipulation of the initial data obtained. In other implementations, the sequences of the data set may be further manipulated, e.g., re-ordered, or homopolymer-compressed; the key pattern is then applied to such derived sequences, and the resulting keys are compared to a reference index whose keys have been similarly manipulated In specific aspects, the keys obtained by applying the key pattern to a data set or a portion of a data set can be reverse-complemented. Preferably, the data set may be reverse complemented and the key pattern applied to obtain the keys. In other instances, the data set may be reverse complemented after the key pattern is applied but before comparison of the keys to a reference index This technique, in which the both the obtained keys and the complement keys (based on the key pattern) are searched within a reference index allows simultaneous searching for candidate locations in both strands of a sequence in a double-stranded molecule, e.g., DNA. Using such a technique effectively allows interrogation of both the forward strand sequence and the reverse strand sequence in a single process step using an index that is roughly half the size of an index containing all possible keys for both strand sequences.

In other specific aspects, the degree of conservation of specific positions within a key pattern can be used to re-order the key to prioritize positions with the highest degree of conservation (and thus likelihood that the position will be included in the key pattern). This is especially useful if there are potentially gaps in the data of the polyoligomer data sets, as the missing data will not then prevent analysis of the available data.

In some implementations, the use of multiple indexes is employed. When the relationships amongst the oligomers of a data set are sufficiently constrained, a single index will often suffice. If relationships amongst the oligomers of a data set are more variable, however, it may be advantageous to use multiple indexes instead of a single index. One example of this would include the use of multiple indexes where each is created using a single key pattern. This enables, for instance, a large range of separation distances while retaining key length/specificity, as discussed further below. Another example is to use multiple subsets of a reference based on key characteristics, e.g., separate indexes for keys beginning with each of the possible nucleotides.

Index Generation

Figure 2:
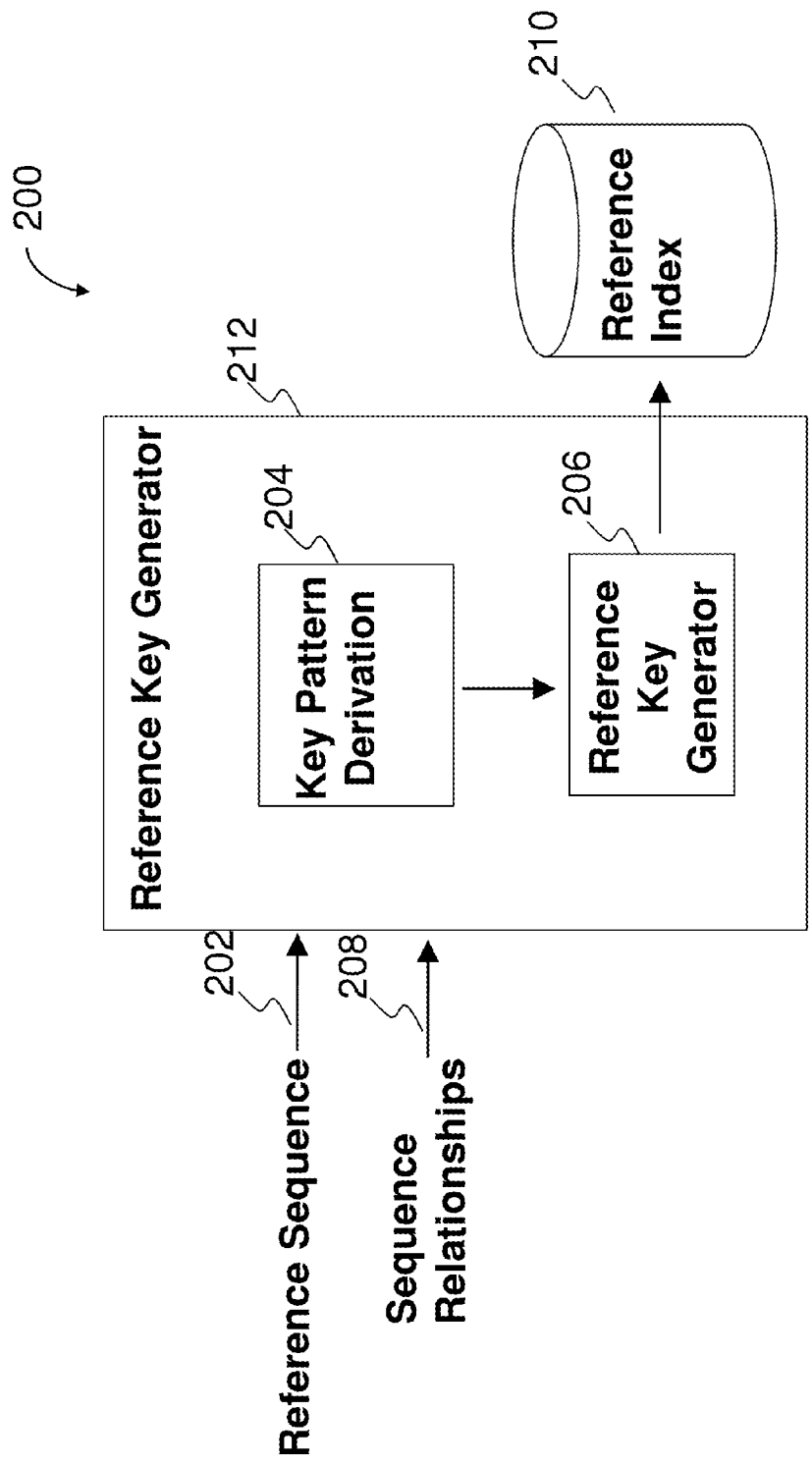
FIG. 2 is a flowchart illustrating an implementation of a process for generating the index.

FIG. 2 is a flowchart illustrating an embodiment of a process for generating the index. Process 200 may be implemented using an index generator such as 154 of FIG. 1B. A reference 202 and potential data set sequence relationships 208 are received by the reference key generator 212. At 204, one or more key patterns are derived, as described further below. At 206, the derived key patterns are applied to the reference to obtain keys in the index for mapping sequence strings to possible locations in the reference. In some embodiments, multiple indexes are generated from multiple key patterns.

Figure 3A:
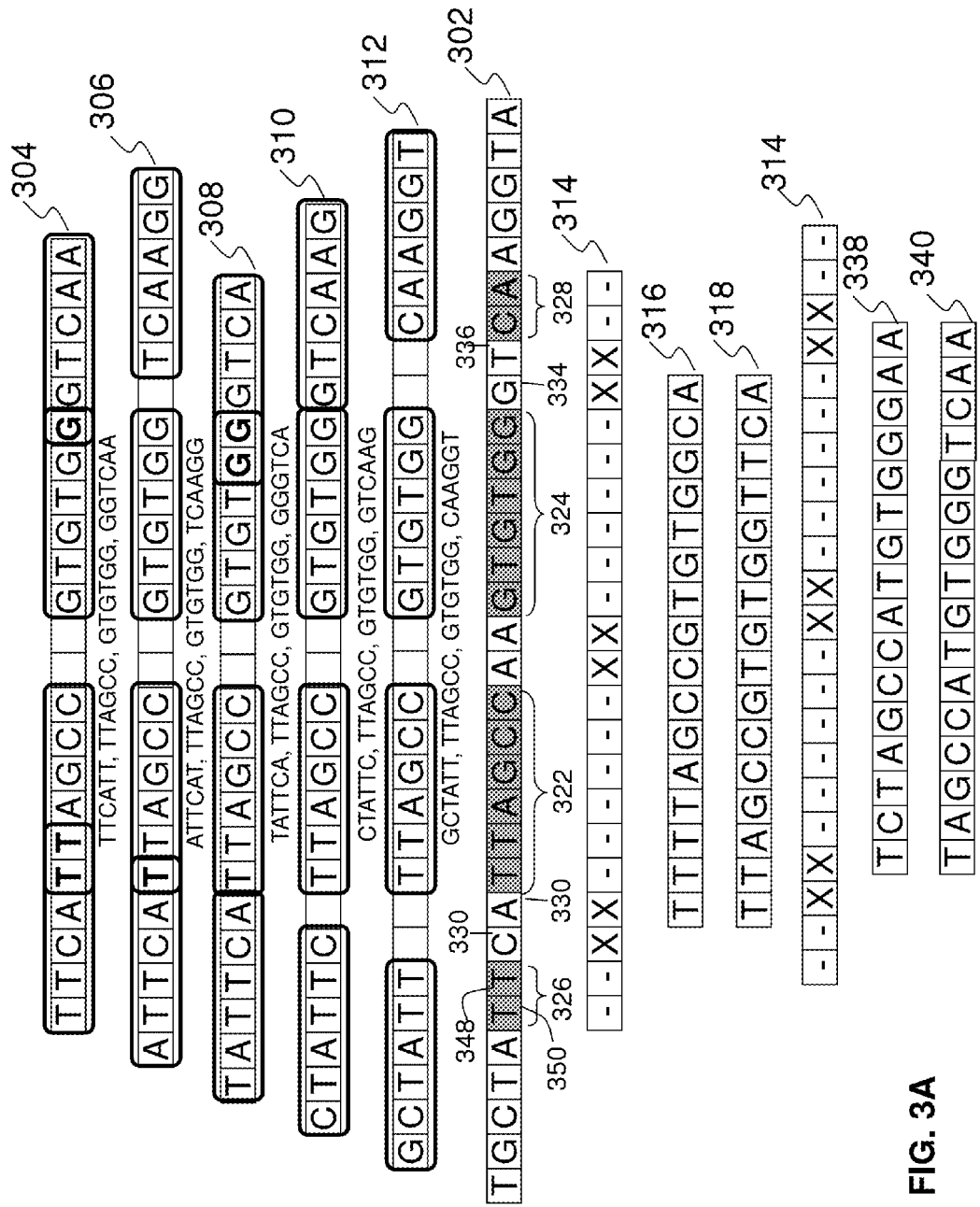
FIGS. 3A-3C are diagrams illustrating examples of key patterns derived from different sets of oligomer sequence relationships.

In some embodiments, once a key pattern is obtained, keys can be generated by repeatedly comparing the key pattern to the reference, each time sliding the key pattern forward by 1 base to a new location on the reference. The key-location mapping data is stored in an index. FIG. 3A exemplifies key generation for use in an index. Assuming that key pattern 314 is initially applied to reference 302 starting at location 350a key 316 is produced for this location. This key can reflect the direct order of sequence within the reference 316, or the bases obtained from the application of the key pattern to the reference may be reordered 318 based on confidence levels to improve mapping performance as described in more detail herein. Advancing along sequence 302 by one base, the key pattern 314 is applied again starting at the next location 348. A new key is produced for the new location, again having either a direct sequence 338 or a re-ordered sequence 340. By repeating the process for the entire length of the reference, each potential location within the reference is mapped to a key.

Figure 3B:
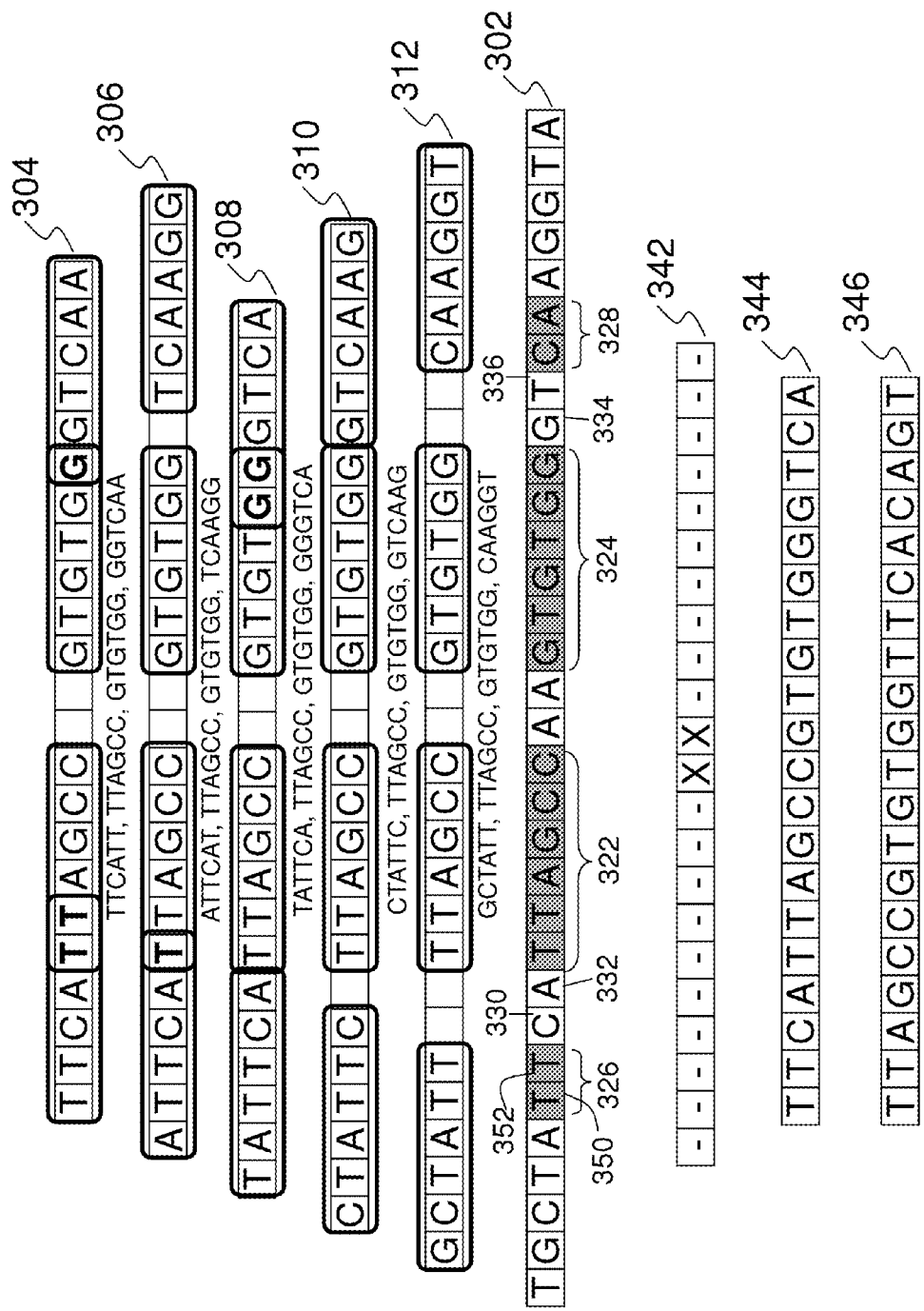
Figure 3C:
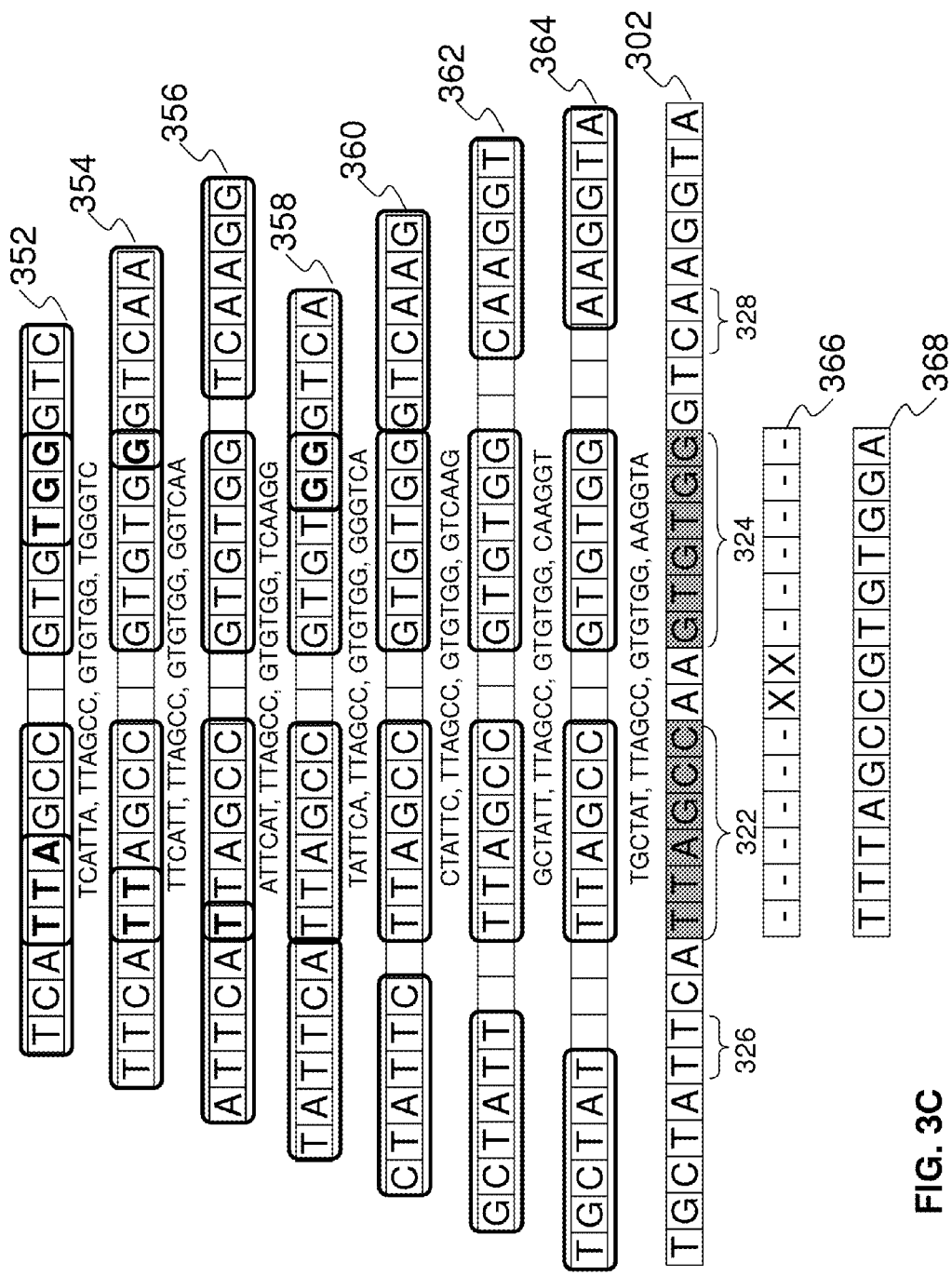

Different key indexes can be generated from a single reference by varying the bases included within the key pattern. For example, in FIG. 3B the key pattern 342 used includes four bases excluded in the key pattern 314 of FIG. 3A. The resulting keys 344, 346 are longer than they keys generated in FIG. 3A, which may be useful for certain mapping implementations. In FIG. 3C, a shorter key pattern 366 is applied to the reference to include only the bases with the highest match confidence to create keys (such as key 368) that can be used when using generated data sets with more variable spacing. Shorter keys, however, generally lead to identification of more potential locations in the reference, so the length of the keys should be balanced by the distribution of separation distances so as not to miss too many of the true mappings without producing an unwieldy number of low-specificity candidate matches.

FIG. 4A is an illustration of an index. In this example, each key-location pair is stored as an entry in index 400. The key strings are in lexical order. It is possible to have keys that correspond to more than one reference location as well as keys that do not correspond to any reference locations (the latter are omitted from the table in some embodiments). To look up a key in the index, a search (such as a linear, binary, or hashed search depending on implementation) based on the key string is performed.

Figure 4B:
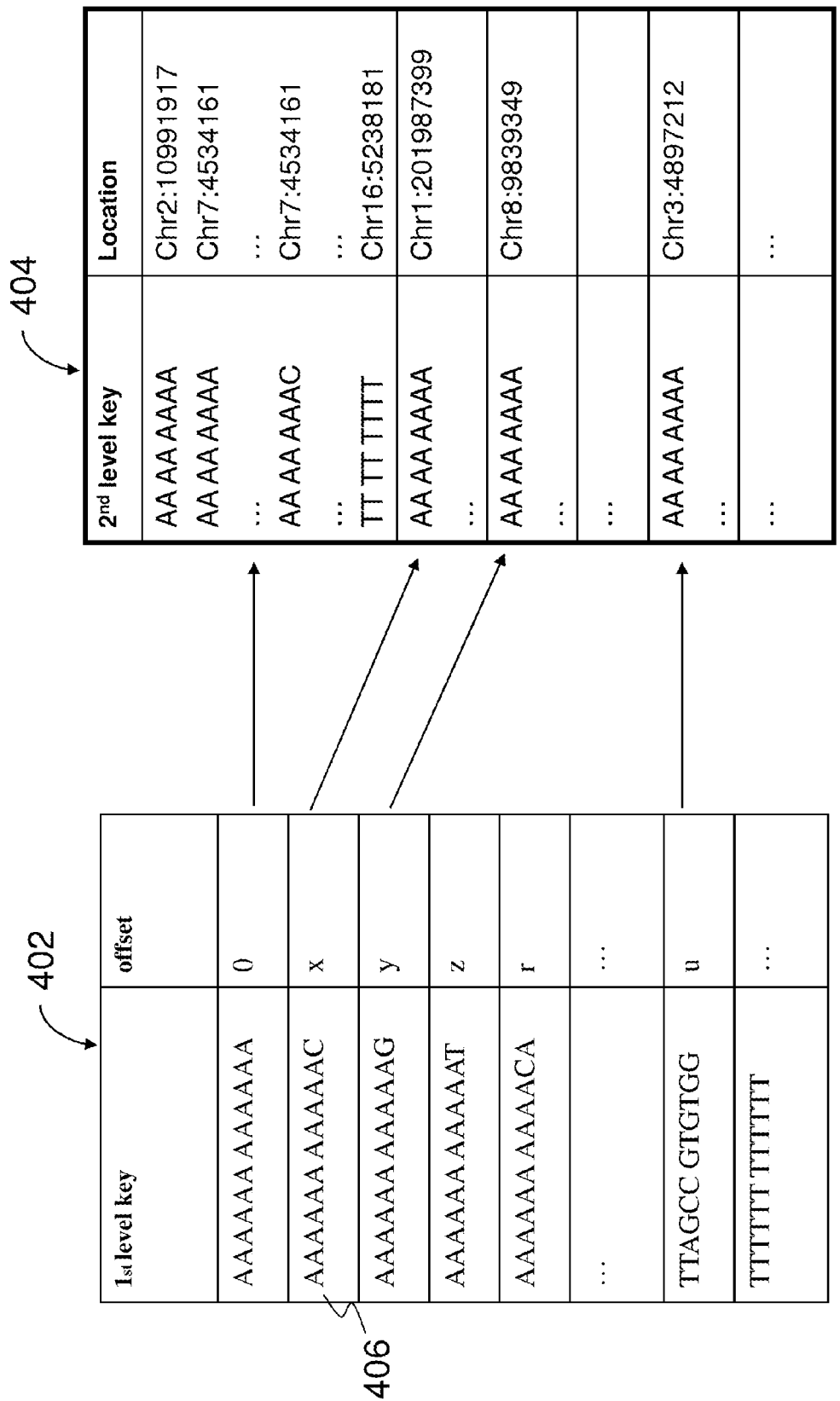
FIG. 4B illustrates another type of an index.

FIG. 4B illustrates another example of an index consisting of two levels or stages designed to increase lookup speed and reduce memory footprint. In this example, each key is split into two portions. The first portion is referred to as the prefix and the second portion is referred to as the suffix. The prefixes are stored according to their lexical order in a first sub-index 402, also referred to as a prefix table. The length of the prefix is chosen based on statistical probabilities, i.e., short enough so that nearly all sequence combinations of that length occur in the reference, and long enough so that the average number of occurrences for each sequence combination meets desired criteria. In this example, the prefix includes 12 bases. Given a prefix length, the length of the suffix depends on the pattern used to generate the key. For example, the suffix length is 4 for reordered keys generated using key pattern 314 (FIG. 3A), and 10 for key pattern 320 (FIG. 3B). The example shows a suffix length of 8. In the prefix table, each entry maps a prefix to an offset of a set of suffixes in a second sub-index 404, also referred to as the suffix table. Each set of suffixes include permutations of bases for the given suffix length. The offset is a value that represents or can be used to derive the base address of the set of suffixes relative to the address at the beginning of the suffix table. In the suffix table, each suffix maps to one or more corresponding reference locations that would generate the key that is the prefix/suffix combination. To find a location in the reference for a given key string, the prefix portion of the key string is identified in the prefix table to obtain the offset. The corresponding set of suffixes can be quickly located in the suffix table using the suffix table base address and the offset. The reference location can be found by looking up the suffix in the suffix set, e.g., by binary search. The suffix lookup is constrained not to exceed the starting location of the next set of suffixes. For example, given prefix 406, the search is restricted to a range between x and y.

Key Pattern Design and Derivation

The design of a key pattern can influence the efficiency, speed and/or computational cost of its use in index generation and mapping. In certain aspects, the oligomer sequences within a data set are individually too short to be used as effective keys on their own, as they will result in information on location that is not sufficiently specific. In other aspects, a longer key may be unnecessarily specific; this may result in an index that doesn't fit in available memory, or requires an excessive computational cost to avoid unacceptable sensitivity to sequencing error or variation between the reference and the sample being sequenced. The shorter the key used the less specific the sequence will be in a reference, and thus the more candidate locations that will be generated by the key. As a general rule, since these candidate locations need to be validated, having a greater number of initial candidate locations will require additional effort to be expended in the validation step. An acceptable key design is thus one in which an appropriate number of candidate locations are determined to allow for validation of these locations at a desired computational cost.

A key pattern may be derived from a corresponding set of oligomer sequence relationships. Examples of such oligomer sequence relationships include expected length(s) of the oligomers, the variation in separation or overlap distance (referred to as distance variation), the statistical distribution of the distance variations amongst oligomer sequences, and the statistical distribution of possible combinations of distance variations within sets of related oligomer sequences.

In some embodiments, the key patterns are derived by comparing possible arrangements of oligomer sequence sets according to the oligomer relationships, and finding conserved positions in the sequences. As will be shown in greater detail in the example below, bases located at the conserved positions can be determined with a high probability for any instantiation of a given set of oligomer sequence relationships. In what follows, we first consider positions which are absolutely conserved and then explain how this can be extended to handle various degrees of conservation. The probability of conservation of a base within a data set may be largely due to the nature of the biochemical process used to obtain the data set. Such information can inform the ordering of the key, as described in more detail herein.

FIG. 3A is a diagram illustrating an example of a key pattern derived from a set of oligomer sequence relationships. In this example, an arbitrary portion of a sample represented by sequence 302 is used to illustrate the key pattern derivation process described in 204 of process 200 (FIG. 2). The oligomer generation process divides the contiguous sequence 302 into a first portion of bases TGCTATTCATTAGCC, and a second portion of bases GTGTGGGTCAAGGTA. The two portions are separated by a fixed distance, in this case a distance of +2 (which are the two bases AA). For purposes of example, the following specification discusses in detail oligomer sequences that are six bases long (referred to as hexamers), although as discussed other oligomer sequence lengths are possible and in some instances preferable. In this example, the oligomer generation process yields two hexamers for each portion, giving a total of four hexamers, with the inner hexamers of each portion assumed to be positioned at the inner ends of the portions, hence separated by two bases (AA). The data generation process is such that the pair of adjacent hexamers obtained from the same sequence portion may have a variable separation or overlap distance, referred to as a distance variation. In this example, the two adjacent hexamers within each portion of 302 are said to have a distance variation of +/−2, which means that the hexamers may be separated by 1 or 2 bases (which corresponds to a distance of 1 or 2, respectively), overlap by 1 or 2 bases (which corresponds to a distance of −1 or −2, respectively), or abut each other without separation or overlap (which corresponds to a distance of 0). In other embodiments, the amount of distance variation may be different.

304-312 are various four-hexamer data sets illustrating the distance variations that may be generated by the biochemical process. As shown, in 304, hexamers TTCATT and TTAGCC have a distance of −2, and hexamers GTGTCG and GGTCAA have a distance of −1. In 306, hexamers ATTCAT and TTAGCC have a distance of −1, while GTGTGG and TCAAGG have a distance of +1. In 308, TATTCA and TTAGCC have a distance of 0 and GTGTGG and GGGTCA have a distance of −2. In 310, CTATTC and TTAGCC have a distance of +1, and GTGTGG and GTCAAG have a distance of 0. In 312, GCTATT and TTAGCC have a distance of 2, as do GTGTGG and CAAGGT.

A set of conserved positions that would make a reasonable key pattern can be determined by a comparison of these arrangements. Certain base positions in sequence 302 are included in the hexamers in any polyoligomer derived from the sequence with the inner two hexamers separated by the two bases AA and a variable data set distance variation of +/−2, regardless of which of the possible separation distance sets is utilized by a given polyoligomer. These conserved positions are shown as shaded regions in sequence 302. In this example, the conserved positions correspond to sequence portions 326, 322, 324, and 328 (TT, TTAGCC, GTGTGG, and CA), which appear in all the hexamer sets 304-312. For a given set of oligomer relationships, the conserved positions correspond to positions in a sequence that are determinable despite different distance variation between sequences. In other words, given a set of oligomer sequences generated from an unknown sequence using a specific (but variable) generation process, the bases of the sequence at the conserved positions will be determined with high probability.

One key pattern that is useful for such oligomer relationships is shown in 314, where the 16 conserved positions of the polyoligomer data set are shown as boxes containing a dash and the non-conserved positions (i.e., positions that cannot be easily determined based on a set of oligomer sequences) are shown as "x". Applying the key pattern to the portion of the reference shown at 302, beginning at position 350, produces key 316, which includes all the bases corresponding to the conserved positions, arranged in the same order as they appear in sequence 302. These bases can be rearranged based on additional probability of conservation to place the bases with the lowest probability of being unspecified in the data set at the beginning of the key string, as shown in key 318.

FIG. 3C is a diagram illustrating another example of a key pattern derived from another set of oligomer sequence relationships. In this example, the adjacent hexamers are known to have a distance variation of +/−3, which means that the hexamers may have a separation or an overlap of up to 3 bases. 352-364 show various possible arrangements of hexamers resulting from sequence 302, including an arrangement in which two adjacent hexamers overlap by 3 bases as shown in 352, and an arrangement in which two adjacent hexamers are separated by 3 bases as shown in 364. A comparison of these arrangements shows that while sequence portions 322 and 324 are still conserved (i.e., appearing in all hexamer arrangements) just as in FIG. 3A, sequence portions 326 and 328 are no longer conserved since the bases in these sequence portions do not appear in all the hexamer sets. The derived key pattern is shown as 364, where the conserved positions are again shown as boxes containing a dash and the non-conserved positions are shown as "x". In this example, key pattern 364 includes 12 conserved positions and is shorter than key pattern 314 of FIG. 3A.

Some tradeoffs exist among possible key patterns. Pattern 364 of FIG. 3C is more inclusive of the possible distance variations than pattern 314 as the former takes into account distances of +3 and −3. Pattern 364 is shorter than pattern 314 since fewer bases are conserved. An index generated based on a shorter pattern such as 364 would allow mapping of oligomer sequence sets with a distance of +3 or −3 to specific locations in the reference, while an index based on pattern 314 would not generally allow mapping in the naïve implementation (though see below). Thus, for a given collection of polyoligomer data sets, a shorter pattern accounting for a greater distance range and having fewer conserved bases leads to a higher portion of oligomer sequence sets being usable. In other words, a higher percentage of the oligomer sequence sets can be mapped to locations in the reference. On the other hand, pattern 364 includes fewer conserved positions than pattern 314 and results in shorter keys that are more likely to be mapped to multiple locations in the reference than a longer key. The identification of more candidate locations will require additional validation on an increased number of locations. Further processing is required in some embodiments to more accurately determine which of the multiple locations can be validated for a given data set, increasing computational cost. Thus, an effectively designed index takes into account these tradeoffs, and employs one or more key patterns designed to be both sufficiently long to avoid generating too many possible locations in the reference and sufficiently succinct to not rule out appropriate sequence relationships.

In some applications, the number of positions that is conserved in all possible instantiations of a polyoligomer dataset may not be enough to provide an acceptably-specific key. Thus, in certain implementations, the requirements for conserved positions are relaxed to obtain a longer key pattern such as key pattern 342 of FIG. 3B. In this example, included in key pattern 342 are bases at positions 330, 332, 334, and 336 (C, A, G, T, respectively), which only occur some of the time in various sets of oligomers. The corresponding sequence portions obtained by applying key pattern 342 to sequence 302 can be provided in the sequential base order of the reference, as in key 344, or attached towards the end of the key as in 346. In the naïve implementation, keys 344 and 346 allow some oligomer sets (such as 304 and 308) to be mapped but not others (such as 306, 310, and 312). It is also more likely for key 342 to map to a unique position in the reference than a shorter key such as 316 or 318. Related issues are discussed further in the following paragraphs.

In some embodiments, certain possible instantiations are simply excluded from the key pattern design as well as from mapping processes. Where statistical information regarding the frequency of various instantiations is available, it may be possible to determine a key pattern of acceptable specificity (length) at the expense of not covering an acceptably small fraction of datasets. For example, it may be that the possible distance variations between two oligomers are −3, −2, −1, 0, +1, +2, and +3. Without knowledge of the corresponding probabilities of occurrence, key pattern 364 shown in FIG. 3C, based on the maximum distance variation of +/−3 bases, might be selected. However, if the corresponding probabilities of occurrence are determined (by empirical measurements, by estimation, or by other techniques) to be 0.05%, 9.95%, 20%, 10%, 35%, and 24.95%, and 0.05%, possible sequence arrangements that have a distance of +3 or −3 might be disregarded, permitting a key pattern based on distance variation of +/−2. Thus, a key pattern 314 shown in FIG. 3A may be used for index generation and distance variations of +/−2 may be used for generation of keys from polyoligomers. In this case, those uncommon polyoligomer sets with a true distance of +3 or −3 will not be correctly instantiated and will fail to map or possibly be mapped incorrectly.

In other embodiments, the longer pattern is again used but instantiations resulting in ambiguous bases are accommodated by generating multiple keys, as described in more detail herein. This may be desirable if the use of the longer pattern without such accommodation results in too large a fraction of data sets not mapping. For those instantiations of a given polyoligomer which leave positions in the key pattern unspecified, bases may be selected based on data quality and/or statistical probability of base conservation, while in other implementations all possible completions of the pattern can be considered, as discussed herein. Examples of "ambiguous bases" includes bases in the data set which are not clearly one of the four expected bases for the data set, e.g., G, A, T, and C for DNA or G, A, U, and C for RNA. An ambiguous position includes an unidentified base, a base that is identified as two or more different bases for a single position in a data set, and the like.

Expanding ambiguous positions in this fashion can result in an exponential increase in compute cost. For this reason as well as others, in some embodiments the bases of a key pattern may be reordered in constructing a key. Some of the possible motivations are as follows.

In the situation just discussed, where the allowed separation distances are such that some portions of a key pattern may be unknown, if the bases selected by the key pattern are reordered to form the final key so that the unknown bases are the last bases of the key (or the least significant bits in terms of index lookup), and the index lookup mechanism is appropriateit is possible to avoid explicit enumeration of the possible completions. In specific situations, the key is effectively shorter (less specific), but only for those instantiations that result in incomplete specification of the key. Even if the goal of placing the unknown bases at the end of the key is not fully realized, a design in which the missing bases affect later positions (lower-order bits) of the key results in better memory locality (improved cache behavior). These situations can be illustrated by FIG. 3A, if we assume that distances of +3 and −3 bases will be considered in generating keys from polyoligomers, but are disregarded when deriving the key pattern. Pattern 314 of FIG. 3A is chosen in this example. Sequence groups 322 (TTAGCC) and 324 (GTGTGG) are more likely to appear in the oligomers since their locations are fixed and do not depend on the distance variation between oligomers. In comparison, sequence groups 326 (TT) and 328 (CA) are less likely to appear because these sequence groups appear in oligomer sequence sets if the distance variation is within +/−2 bases but do not always appear if the distance is +3 or −3 bases. Thus, key 318 is generated, with sequence groups 322 and 324 placed at the beginning of the key, and sequence groups 326 and 328 appended after portions 322 and 324 in the key since groups 322 and 324 are more likely to appear in keys derived from sequence sets than 326 and 328. When using the resulting index to map a polyoligomer with separation distances allowed to range over +/−3, some bases of the key will be unspecified in some instantiations of the polyoligomer. For certain instantiations (in the example, separation distance within +/−2 on the left, and separation distance −3 on the right), the unspecified base is the last base of the key, so we do not need to enumerate the possible values. In others, one or two of the final four bases of the key may be unspecified. Due to reordering, the first twelve bases of the key will always be determined by the inner hexamers, hence retaining better specificity in the former approach and yielding better locality of multiple index lookups in the latter.

In some embodiments, reordering the bases of the key may have additional advantages even when all positions within the key are specified in all allowed separation relationships. A plurality of different keys for a single polyoligomer set may be obtained from a single key pattern, corresponding to instantiation with different possible separation relationships. Even where all bases of the key pattern are specified in all keys, certain bases of the pattern are modified less than others. If the bases of the key pattern are reordered to place the more-constant bases first in the key, better locality (cache performance) can be achieved across the set of index lookups for a given data set. This can be illustrated by FIG. 3A. Due to the requirement that the inner two hexamers be separated by precisely two bases, the same twelve bases can be made to occupy the same positions in all keys derived from a single polyoligomer. Reordering the bases of key pattern 314 such that segments 322 and 324 are placed at the beginning of the key, so that sequence 302 gives rise to key 318, is an illustration of this concept. In some embodiments, this is taken further; keys are generated from a single data set and key pattern by examining sequence relationships in an order that improves locality among index lookups. By enumerating sequence relationship possibilities in certain orders, the more significant bits of the keys change less often. Referring to FIG. 3A, if the final order of bases in the key for sequence 302 is 322+324+326+328, giving rise to keys such as 318, e.g., it will be preferable to enumerate the possible separation relationships for a polyoligomer data set by considering all possible separations of the oligomers in the right portion together for each possible separation within the left portion; this will lead to considering all keys sharing the first 14 bases in a group. Whereas, inverting the process to consider all possible separations of the left portion together for each possible separation of the right portion will lead to considering keys sharing the first 12 and the last 2 bases in a group. For some embodiments of the reference index, the former will give better locality.

Oligomer Sequence Mapping

Figure 5:
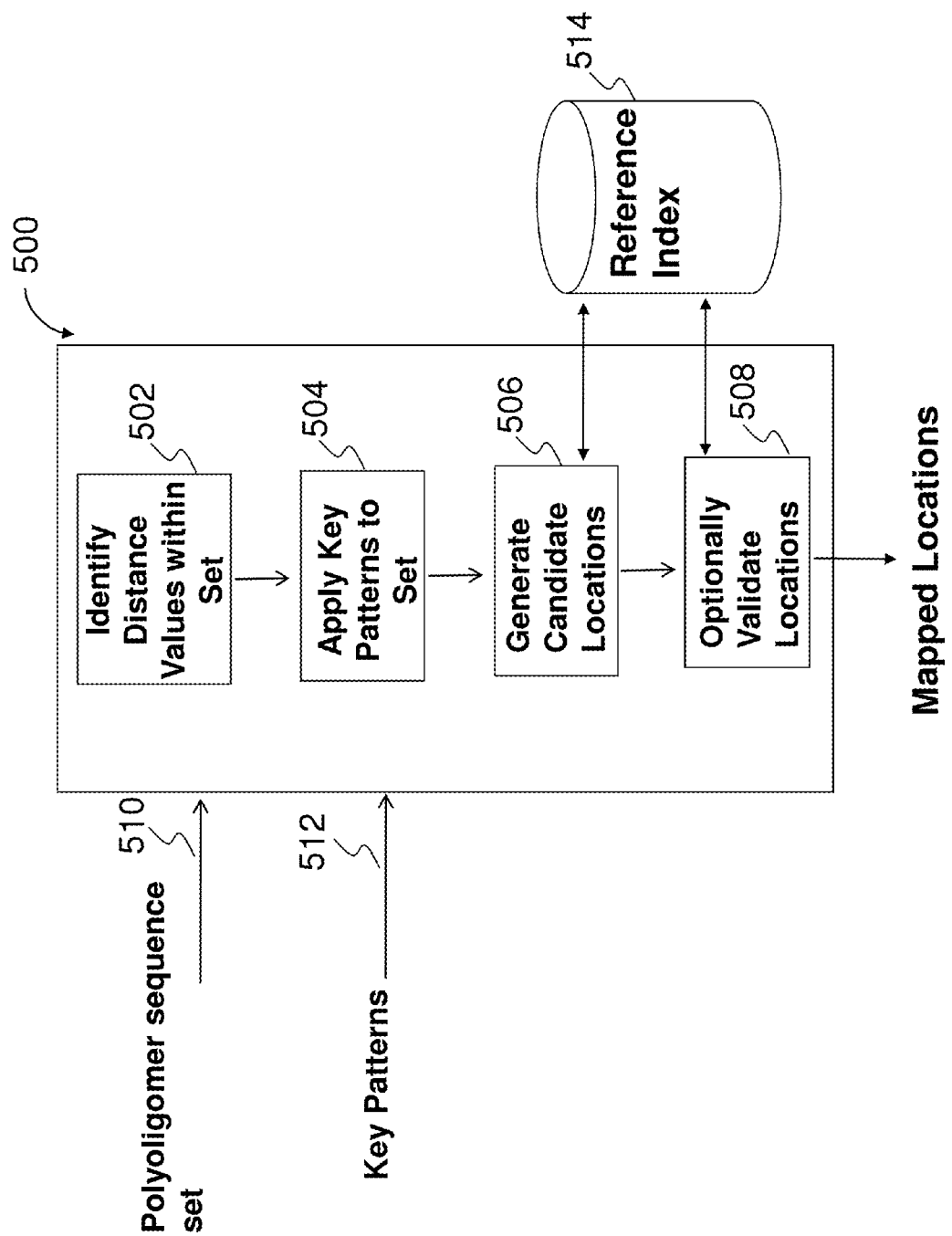
FIG. 5 is a flowchart illustrating an implementation of a process for mapping oligomer sequences.

Once an index is generated, it can be used to map oligomer sequences obtained from samples using the key patterns used to produce the index. FIG. 5 is a flowchart illustrating an implementation of a process for mapping oligomer sequences. Process 500 may be implemented on an oligomer mapping system such as that illustrated in FIG. 1 at 100. At 502, a data set of related oligomer sequences (510) are received. At 504, one or more key patterns (512) derived from a set of oligomer relationships are applied to a polyoligomer data set to obtain one or more keys that are consistent with the data set. The one or more keys are located (506) in a reference index (514) configured to map possible keys to their respective candidate locations in the reference. The reference index may be generated as illustrated in FIG. 2. The identified candidate locations are optionally validated (508), either using the index (514) as shown, or through other means. For example, the candidate locations can be validated by comparing the sequence at a candidate location of the reference to possible instantiations of the complete sequences of the polyoligomer. The successfully mapped location(s) are optionally output and may be used for genetic analysis, subsequent software processing, and many other applications. For example, the location(s) are used in some embodiments to assemble a new sequence/genome assembly. In some embodiments, the locations are used to detect novel sequences.

Figure 6:
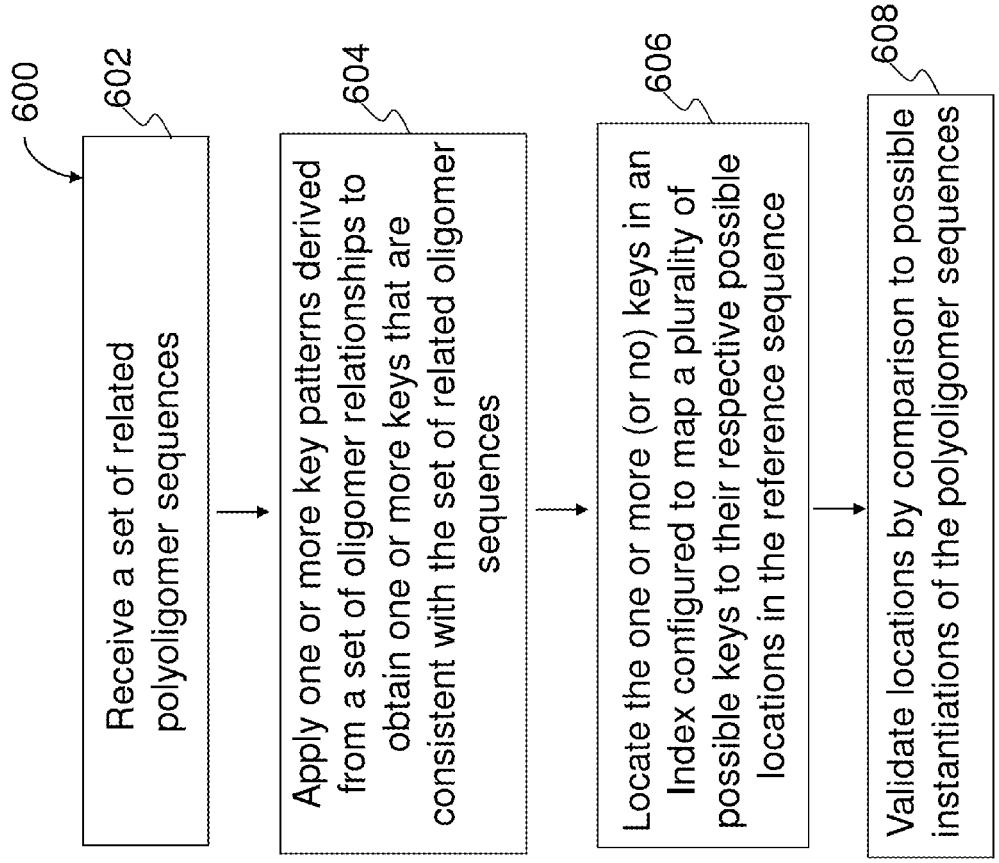
FIG. 6 is a flowchart illustrating a process for obtaining keys that are consistent with a given set of related oligomer sequences.

FIG. 6 is a flowchart illustrating an implementation of a process for obtaining keys that are consistent with a given set of related oligomer sequences. In some embodiments, process 600 is used to implement process 500 (FIG. 5). At 602, one or more distance values that could have existed between at least some of the given set of oligomer sequences are selected. At 604, these possible distance values are used to instantiate the data set. One or more key patterns, based on the inputs of the sequence set 610 and the reference 608, are applied to these possible instantiated sequences with the selected distance values to obtain one or more corresponding keys. These keys can be compared to those in the appropriate index 606 to identify possible locations.

Figure 7:
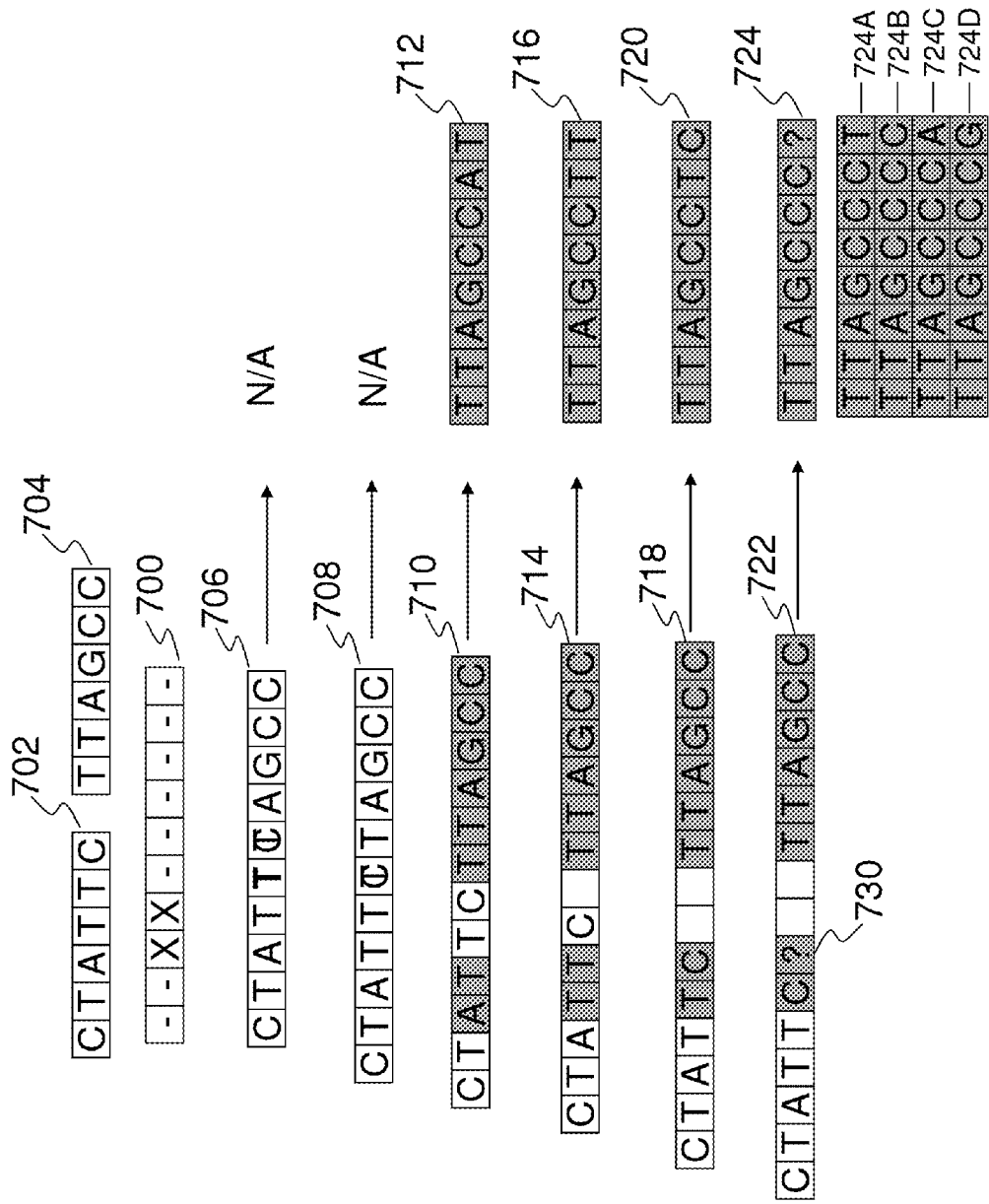
FIG. 7 is a sequence diagram illustrating an example of obtaining keys that are consistent with a given set of related oligomer sequences, using a process similar to 600.

FIG. 7 is a sequence diagram illustrating an example of obtaining keys that are consistent with a given set of related oligomer sequences, using a process similar to 600. For purposes of illustration, the example shows a partial key pattern 700 and a partial set of two adjacent, related hexamers 702 and 704. A complete key pattern and a full set of related oligomers are used in practice. Here, key pattern 700 includes 2 conserved positions, followed by 2 non-conserved positions, followed by 6 conserved positions. Furthermore, the last base of the pattern is constrained to correspond to the last base of the second hexamer. Selective distance values and possible sequences are evaluated to determine whether hexamers 702 and 704 can be generated from such sequences. 706 shows the two hexamers overlapping by two bases. Since the end of hexamers 702 and the beginning of 704 (TC and TT, respectively) do not match perfectly when overlapped by 2, it is impossible for the distance between the hexamers to be −2, unless there is an error in the data set in one of the two conflicting bases. Had the end of hexamer 702 been TT instead of TC, a distance of −2 would have been feasible. 708 shows that it is also impossible for the distance to be −1 due to the mismatched end bases (C for 702 and T for 704). It is possible, however, for the hexamers to have a distance of 0, 1, 2, or 3 and forming sequences 710, 712, 718, and 722, respectively. The instantiations from the data set can then be reordered to place the bases with the lower quality scores at the back of the key, forming reordered keys 712, 716, 720, and 724. Due to the fact that sequence 722 has one unknown position, there are four potential instantiations for 724, one with each of the four bases at the unknown position. Thus, this instantiation is either disallowed or the missing position is filled in with all possible values to create substituted keys, as shown in 724A-D. Locations in the reference can be looked up in the index using these keys.

In some embodiments, statistical distribution information about distance combinations within a set of related oligomer sequences can be used to limit computation. The information is used to include or exclude certain instantiations of a data set. For example, if it is known that when there is a distance of +1 between the first pair of oligomers, there is a 99.9% chance that there is a distance of 0 between the second pair of oligomers, sequence arrangements assigning a distance of +1 between the first pair and a non-zero distance to the second pair could therefore be omitted for the purpose of deriving keys from each data set.

Figure 8A:
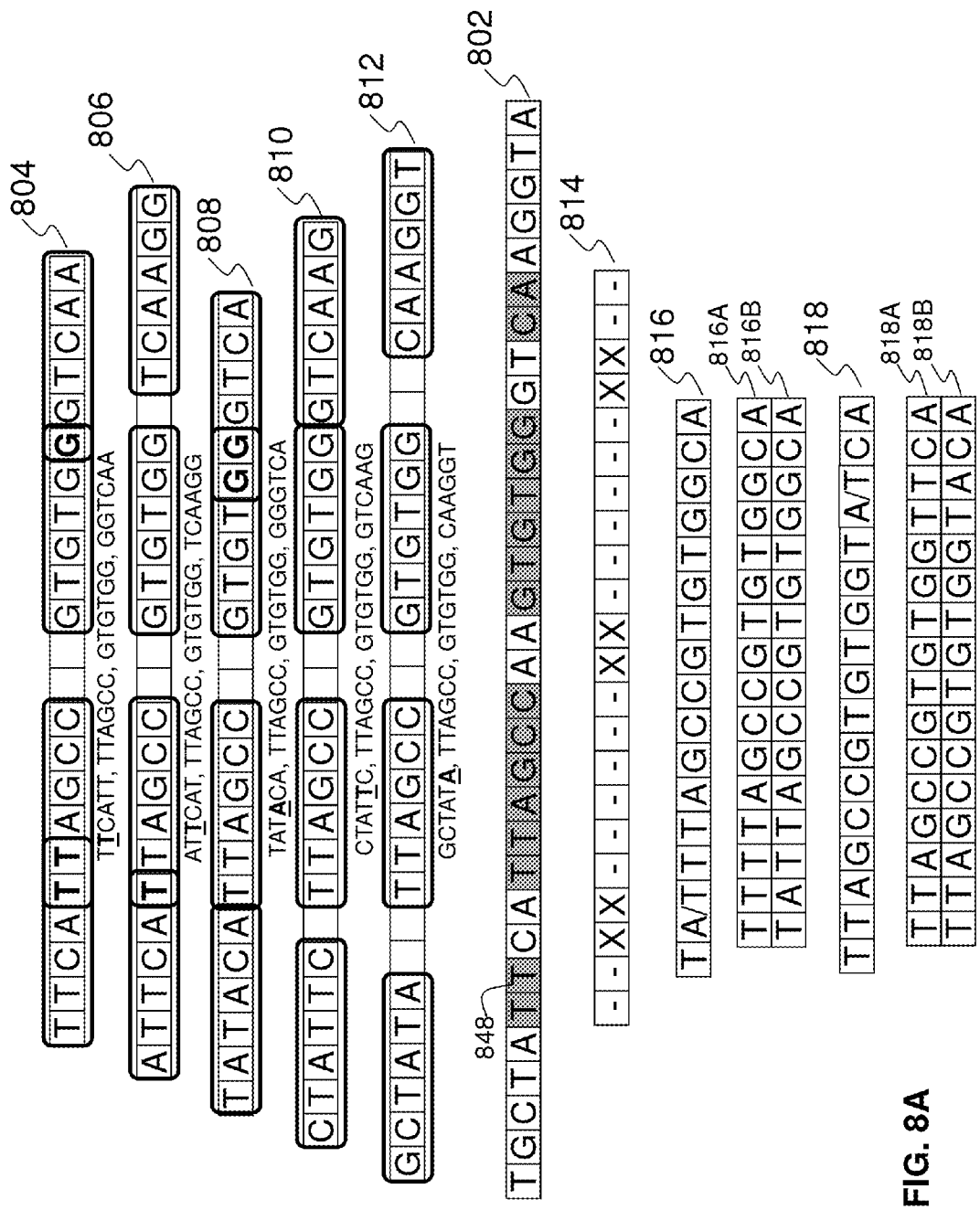

In other embodiments, obtained polyoligomer data sets corresponding to the same mapping region may have one or more positions in the oligomer sets that are not clear data points, referred to herein as "ambiguous" bases or positions, such as those illustrated in FIGS. 8A through 8E. In FIG. 8A, a polyoligomer data set having sets 802, 804, 806, 808 and 812, which are all individually complete oligomers. Although these bases should have consistently conserved positions when key 814 is applied, as in FIG. 3A, here there is a discrepancy between the data sets, with sets 804, 806 and 810 having a "T" at position 848 in the reference, and sets 808 and 812 having an "A" at position 848. Instead of searching the index for a key with a base missing, as illustrated in sequential key 816 and reordered key 818, the mapping operation can be carried out for each of the two potential variations, A and T, as shown in substituted sequential keys 816A and 816B and substituted reordered keys 818A and 818B.

Figure 8B:
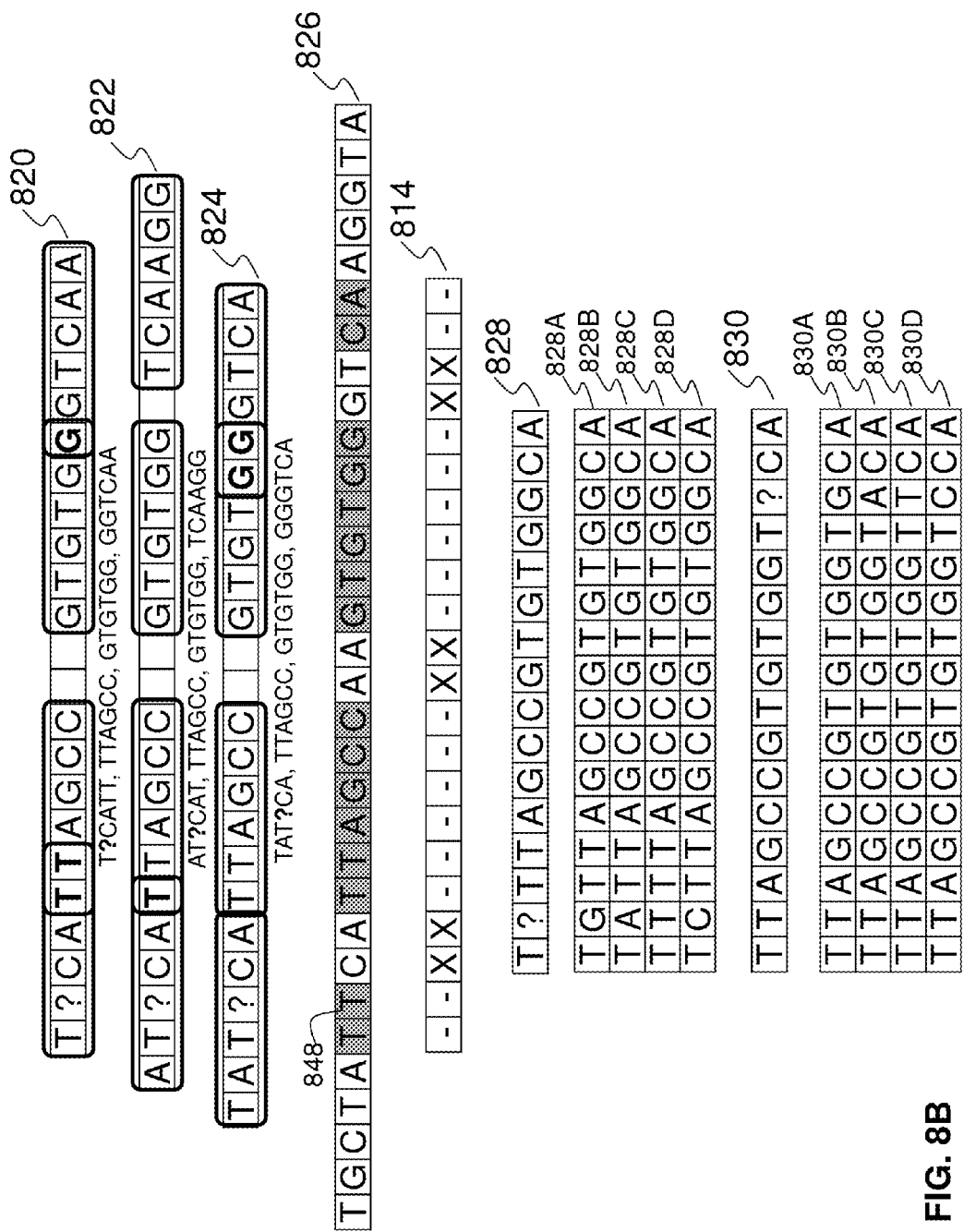

In other examples, an unidentified position may be substituted with each of the potential bases, resulting in four possible keys for each unidentified position in a polyoligomer data set. FIG. 8B illustrates a scenario in which position 848 in the obtained polyoligomer data sets is completely unidentified, and therefore may be any of the four bases. The key 814 applied to these data sets results in a key of 16 bases, with 14 contiguous bases and one unknown base, illustrated as sequential key 828 and reordered key 830. Rather than use only the 14 contiguous bases to map the data in the index, the index may be searched in four separate operations using the keys 828A-D or 830A-D, which respectively correspond to substituted keys having 16 contiguous bases that represent all of the possible combinations of the unidentified base in the initial key.

Figure 8C:
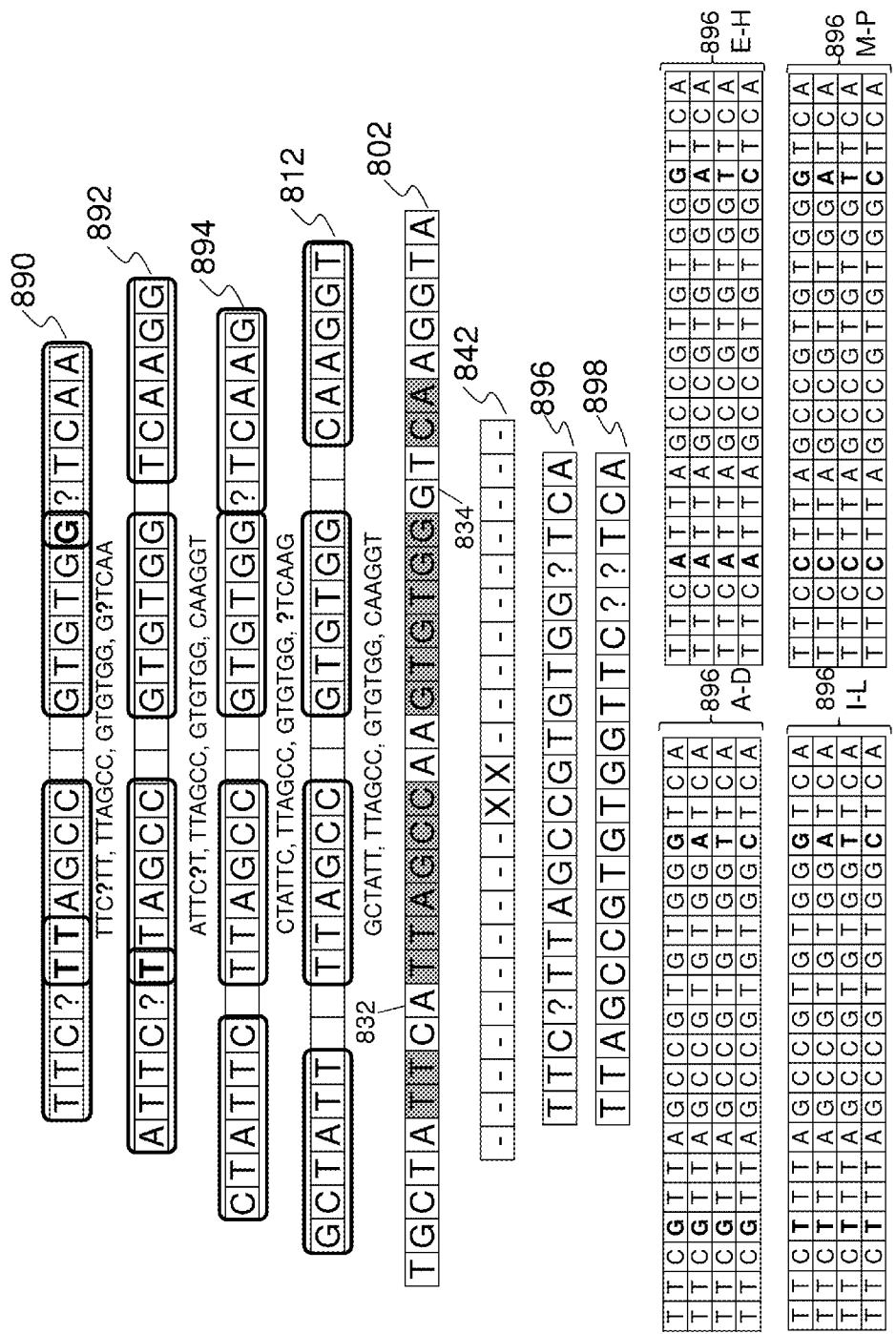
Figure 8D:
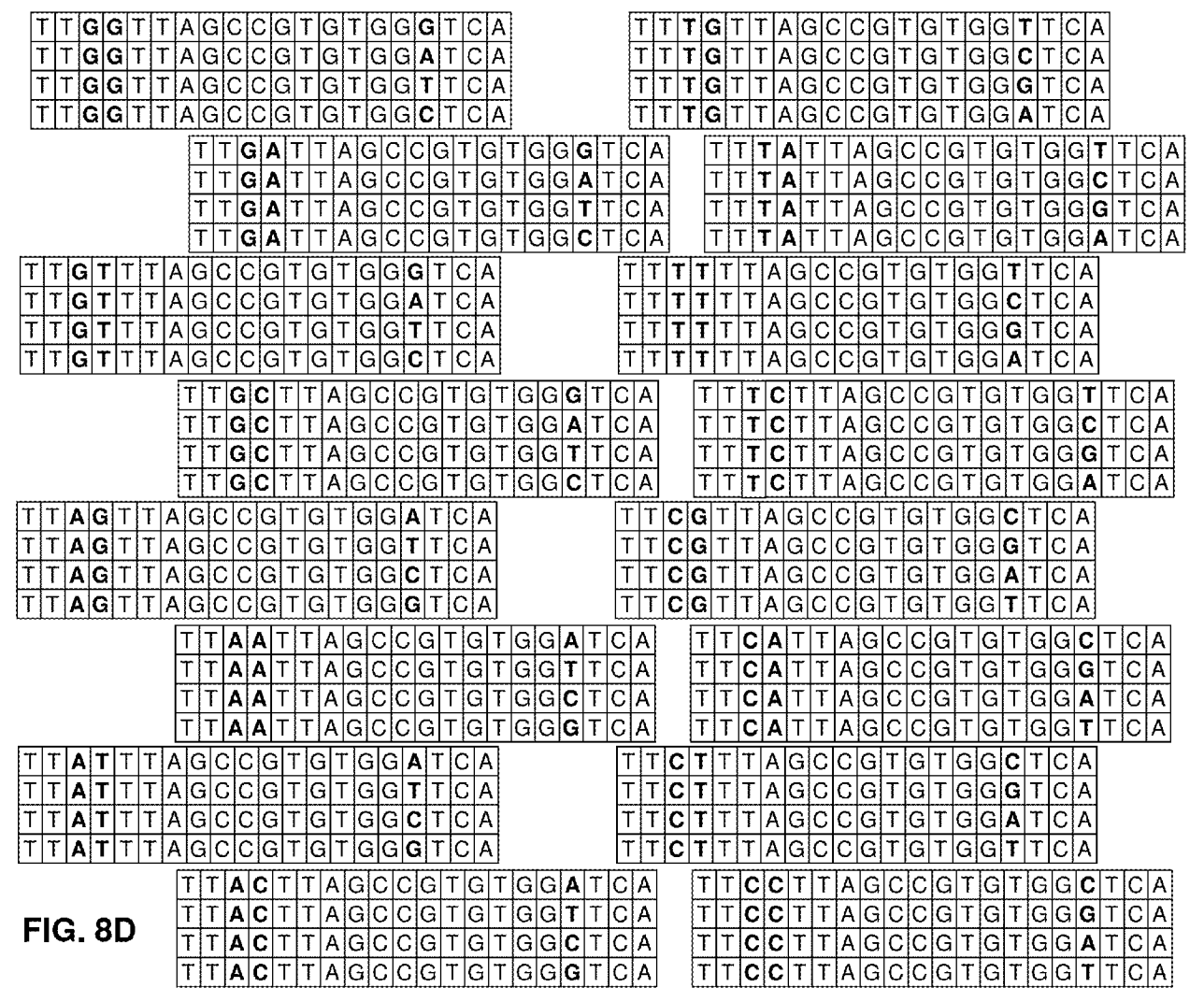

The use of multiple predicted keys generated from a polyoligomer data set to map potential locations in a reference index can be used to map data sets having two or more ambiguous or unidentified bases within a single data set. FIGS. 8C and 8D illustrate the use of multiple keys that may be generated from polyoligomer data sets having two unidentified bases when key pattern 842 is applied to the data set (890, 892, 894 and 812). In this example, application of key pattern 842 results in two unidentified bases at positions 832 and 834 in reference 802. When key pattern 842 is applied to the polyoligomer data set, the initial keys that are generated have two unidentified positions, as shown in sequential key 896 and reordered key 898.

With multiple unidentified positions in a key, there are $4^n$ different potential keys that could be used to map the data set in an index, with n= the number of unidentified positions. The use of a large number of instantiations will need to be balanced against computer cost, likelihood for ambiguous or incorrect mapping data or technical cost for re-obtaining the data sets. In certain circumstances, it may be preferable to search the multiple keys, and FIG. 8C illustrates the sequential keys 896 A-P that would be generated for two unidentified positions using key pattern 842, with each of the variable positions highlighted in bold. FIG. 8D illustrates the potential permutations if an additional third position were ambiguous, with a total of three unidentified bases in the initial key. This would result in $4^3$ or 64 possible substituted keys, which are set forth in 8D with the variable positions highlighted in bold.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of generating an index, the index operable to determine where, in a reference sequence, a data set of one or more related oligomer sequences maps to the reference sequence, the oligomer sequences of the data set obtained from a same fragment of genetic material, the method comprising:

applying, with a computer system, a key pattern to the reference sequence to generate a plurality of keys, wherein the key pattern includes a first set of N contiguous positions separated by K positions from a second set of M contiguous positions, the separation being based on predicted relationships between oligomer sequences of the data set, wherein the key pattern is defined by predetermined values for N, K and M, the applying including:

applying the key pattern to a first location of the reference sequence to obtain a first set of bases, the first set of bases including:

N contiguous bases of the reference sequence starting from the first location, and M contiguous bases of the reference sequence starting from N+K positions after the first location, N, M, and K being integers greater than or equal to one;

using the first set of bases to generate a first key;

applying the key pattern to a plurality of other locations to generate other keys, wherein the applying of the key pattern to the first and other locations uses the same values for N, M, and K; and storing the keys in the index, the index being stored in a searchable computer readable medium;

wherein each key corresponds to one or more possible locations within the reference sequence.

2. The method of claim 1, wherein the predicted sequence relationships comprise both variable and fixed separation distances between sequences of the data set.

3. The method of claim 1, wherein the keys are generated by applying the key pattern using sequential base key generation.

4. The method of claim 3, wherein the key pattern is sequentially forwarded on the reference sequence by a single base.

5. The method of claim 1, wherein the index comprises keys generated using one or more genomic sequences as the reference sequence.

6. The method of claim 5, wherein the one or more genomic sequences comprise a human sequence.

7. The method of claim 5, wherein the one or more genomic sequences comprise substantially an entire genome.

8. The method of claim 1, wherein the reference sequence comprises an RNA or cDNA sequence.

9. The method of claim 8, wherein the RNA or cDNA sequence comprises a human sequence.

10. The method of claim 1, wherein the reference sequence includes two or more variations of a single reference sequence.

11. The method of claim 1, wherein the index includes keys generated from two or more references sequences.

12. The method of claim 1, wherein the predicted relationships between sequences of the data set are based in part on statistical distribution information for conserved positions in the data set.

13. The method of claim 12, wherein the statistical distribution information includes a predicted distribution of distances between two or more adjacent oligomers.

14. The method of claim 12, wherein the statistical distribution information includes a predicted distribution of distance combinations within a set of related oligomers.

15. The method of claim 1, wherein the key pattern has a pattern length sufficiently long to avoid generating an undesired number of candidate locations in the reference sequence.

16. The method of claim 1, wherein the index comprises keys having bases in a sequential order of the reference sequence.

17. The method of claim 1, wherein the index includes two or more sub-indexes.

18. The method of claim 17, wherein the index includes a prefix index.

19. The method of claim 18, wherein the entries in the prefix index map to a plurality of offsets in a sub-index.

20. The method of claim 17, wherein the index further includes a suffix index.

21. The method of claim 20, wherein the entries in the suffix index map to a plurality of possible locations in the reference sequence.

22. The method of claim 1, further comprising:
modifying the first key by reordering a sequence of bases in the first key before storing the first key in the index.

23. The method of claim 1, further comprising:
comparing sequences of the data set to the plurality of keys to map the sequences to the reference sequence.

24. The method of claim 1, wherein the predicted sequence relationships include at least one variable separation distance between two oligomer sequences of the data set.

25. The method of claim 1, wherein the index stores the keys ordered by bases at one or more positions in the keys.

26. The method of claim 25, wherein the keys are in lexical order.

27. A system for generating an index for oligomer sequence analysis, the index operable to determine where, in a reference sequence, a data set of one or more related oligomer sequences maps to the reference sequence, the oligomer sequences of the data set obtained from a same fragment of genetic material, the system comprising:
an interface configured to receive the reference sequence; and
a processor coupled to the interface, the processor configured to apply a key pattern to the reference sequence to obtain a plurality of keys for storing in the index,
wherein the key pattern includes a first set of N contiguous positions separated by K positions from a second set of M contiguous positions, the separation being based on predicted relationships between oligomer sequences of the data set wherein the key pattern is defined by predetermined values for N, K and M, the applying including:
applying the key pattern to a first location of the reference sequence to obtain a first set of bases, the first set of bases including:
N contiguous bases of the reference sequence starting from the first location, and
M contiguous bases of the reference sequence starting from N+K positions after the first location, N, M, and K being integers greater than or equal to one;
using the first set of bases to generate a first key;
applying the key pattern to a plurality of other locations to generate other keys, wherein the applying of the key pattern to the first and other locations uses the same values for N, M, and K,
wherein the keys correspond to possible locations in the reference sequence.

28. A computer program product for generating an index, the index operable to determine where, in a reference sequence, a data set of one or more related oligomer sequences maps to the reference sequence, the oligomer sequences of the data set obtained from a same fragment of genetic material, the computer program product being embodied in a non-transitory computer readable medium and comprising computer instructions for:
receiving a reference sequence; and
applying a key pattern to the reference sequence to obtain a plurality of keys for storing in the index,
wherein the key pattern includes a first set of N contiguous positions separated by K positions from a second set of M contiguous positions, the separation being based on predicted relationships between oligomer sequences of the data set wherein the key pattern is defined by predetermined values for N, K and M, the applying including:
applying the key pattern to a first location of the reference sequence to obtain a first set of bases, the first set of bases including:
N contiguous bases of the reference sequence starting from the first location, and
M contiguous bases of the reference sequence starting from N+K positions after the first location, N, M, and K being integers greater than or equal to one;
using the first set of bases to generate a first key;
applying the key pattern to a plurality of other locations to generate other keys, wherein the applying of the key pattern to the first and other locations uses the same values for N, M, and K,
wherein the keys correspond to possible locations in the reference sequence.

* * * * *

UNITED STATES PATENT AND TRADEMARK OFFICE
CERTIFICATE OF CORRECTION

PATENT NO. : 8,738,296 B2
APPLICATION NO. : 12/698986
DATED : May 27, 2014
INVENTOR(S) : Aaron L. Halpern and Igor Nazarenko It is certified that error appears in the above-identified patent and that said Letters Patent is hereby corrected as shown below:

In the Claims

In Claim 19, column 41, lines 38, please delete the word "the" between "wherein" and "entries" so that the line reads:

The method of claim 18, wherein entries in the

In Claim 21, column 41, lines 42, please delete the word "the" between "wherein" and "entries" so that the line reads:

The method of claim 20, wherein entries in the

Signed and Sealed this
Twelfth Day of January, 2016

Michelle K. Lee
*Director of the United States Patent and Trademark Office*